(12) United States Patent
Gwag et al.

(10) Patent No.: US 7,371,896 B2
(45) Date of Patent: *May 13, 2008

(54) TETRAFLUOROBENZYL DERIVATIVES AND PHARMACEUTICAL COMPOSITION FOR PREVENTING AND TREATING ACUTE AND CHRONIC NEURODEGENERATIVE DISEASES IN CENTRAL NERVOUS SYSTEM CONTAINING THE SAME

(75) Inventors: Byoung-Joo Gwag, Suwon-si (KR); Sung-Hwa Yoon, Suwon-si (KR); Ho-Sang Moon, Suwon-si (KR); Eun-Chan Park, Suwon-si (KR); Seok-Joon Won, Suwon-si (KR); Young-Ae Lee, Suwon-si (KR); Hae-Un Lee, Suwon-si (KR)

(73) Assignee: AmKor Pharma, Inc., Seattle, WA (US)

( * ) Notice: Subject to any disclaimer, the term of this patent is extended or adjusted under 35 U.S.C. 154(b) by 43 days.

This patent is subject to a terminal disclaimer.

(21) Appl. No.: 11/450,596

(22) Filed: Jun. 8, 2006

(65) Prior Publication Data

US 2006/0235239 A1    Oct. 19, 2006

Related U.S. Application Data

(62) Division of application No. 11/165,293, filed on Jun. 22, 2005, now Pat. No. 7,189,878, which is a division of application No. 10/481,648, filed as application No. PCT/KR03/01205 on Jun. 19, 2003, now Pat. No. 6,927,303.

(30) Foreign Application Priority Data

Jun. 19, 2002   (KR) ................. 10-2002-34259

(51) Int. Cl.
*C07C 229/00* (2006.01)
(52) U.S. Cl. .................. 562/457; 562/458; 560/48; 560/47
(58) Field of Classification Search .............. None
See application file for complete search history.

(56) References Cited

U.S. PATENT DOCUMENTS 3,632,760 A   1/1972   Shen et al. ............. 514/166

(Continued)

FOREIGN PATENT DOCUMENTS

DE         2031227        1/1971

(Continued)

OTHER PUBLICATIONS

Lehninger et al., Principles of Biochemistry, 2nd. ed. 384-390, 1993.

(Continued)

*Primary Examiner*—Karl Puttlitz
(74) *Attorney, Agent, or Firm*—Seed IP Law Group PLLC

(57) ABSTRACT

The present invention relates to a tetrafluorobenzyl derivative and a pharmaceutical composition for prevention and treatment of acute and chronic neurodegenerative disease in central nervous system and ophthalmic diseases containing the same. The tetrafluorobenzyl derivative of the present invention can effectively be used to prevent and treat chronic neurodegenerative diseases such as Alzheimer's disease, Parkinson's disease and Huntington's disease, degenerative brain disease such as epilepsy and ischemic brain disease such as stroke.

15 Claims, 15 Drawing Sheets

U.S. PATENT DOCUMENTS

| | | | | |
|---|---|---|---|---|
| 3,674,844 | A | 7/1972 | Shen et al. | 562/440 |
| 5,434,163 | A | 7/1995 | Edlind et al. | 514/310 |
| 5,527,814 | A | 6/1996 | Louvel | 514/367 |
| 6,136,835 | A | 10/2000 | Camden | 514/383 |
| 6,358,945 | B1 | 3/2002 | Breitfelder et al. | 514/227 |
| 6,573,402 | B1 | 6/2003 | Gwag et al. | 562/435 |

FOREIGN PATENT DOCUMENTS

| | | |
|---|---|---|
| EP | 122827 A1 | 10/1984 |
| GB | 1268465 | 3/1972 |
| JP | 54-125632 A | 9/1979 |
| JP | 60-237041 A | 11/1985 |
| JP | 2000-212141 | 8/2000 |
| JP | 2000-273041 | 10/2000 |
| WO | WO 86/03199 | 6/1986 |
| WO | WO 94/13663 | 6/1994 |
| WO | WO 99/01421 | 1/1999 |

OTHER PUBLICATIONS

Anderson, D.K. et al., Ann. Emerg. Med. 22:987-992 (1993).
Anderson, W.W. et al., J. Neurophysiol. 57:1-21 (1987).
Beal, M.F. et al, J.Neurosci. 11:1649-1659 (1991).
Beal, M.F. et al., Nature 321: 168-171 (1986).
Beal, M.F., Ann. Neurol. 38:357-366 (1995).
Benveniste, H et al., *J. Neurochem*, 43(5):1369-1374 (1984).
Brouillet, E. et al.. Neuroreport. 4:387-390 (1993).
Browne, S.E. et al., Brain Pathol. 9:147-163 (1999).
Bush, A.I. et al., Science 265:1464-1467 (1994).
Chan, P. H. *J. Neurotrauma.*, 9 Suppl 2:S417-423 (1992).
Chan, P.H., Stroke 27:1124-1129 (1996).
Choi, D.W. et al., J Neurosci. 7:369-379, 1987.
Choi, D.W. et al., Annu Rev Neurosci 13:171-182 (1990).
Choi, D.W. et al., Annu. Rev. Neursci 21:347-375 (1988).
Choi, D.W. et al., Journal of Neuroscience 7(2): 357-368 (1987).
Choi, D.W., Neuron 1:623-634 (1988).
Cuajungco, M.P. et al., Brain Research Reviews 23:219-236 (1997).
Demediuk, P. et al., J. Neurochem. 52:1529-1536 (1989).
Dexter, D. T. et al., *Ann Neurol.*, 32 Suppl:S94-100 (1992).
Dingledine, R. et al., Trends Pharmacol. Sci. 11:334-338 (1990).
Eisen, A. et al., Drugs Aging 14:173-196 (1999).
Faden, A.I. et al, Science 244:798-800 (1989).
Faden, A.I. et al., J. Neurotrauma. 5:33-45 (1988).
Faden, A.I., Pharmacol. Toxicol. 78:12-17 (1996).
Fahn, S. and Cohen, G., *Ann. Neurol.*, 32(6):804-812 (1992).
Ferrante, R. J. et al., *Science*, 230(4625):561-563 (1985).
Fischer-Nielsen, A. et al., *Free Radic Biol Med*. 13(2): 121-126 (1992).
Flamm, E. S. et al., *Stroke*, 9(5):445-447 (1978).
Frederickson, C. J. and Bush, A. I., *Biometals*, 14:353-366 (2001).
Frederickson, C.J. et al., Brain Res. 480:317-321 (1989).
Gerlach, M. et al., *Journal of Neurochemistry* 63: 793-807 (1994).
Gilgun-Sherki, Y. et al., *Pharmacological Reviews* 54: 271-284 (2002).
Goldberg, M. P. et al. *J. Pharmac. Exp. Ther.*, 243:784-791 (1987).
Goldberg, M.P. et al., J Neurosci. 13:3510-3524 (1993).
Goodman & Gilman's The Pharmacological Basis of Therapeutics, Joel G. Hardman et al., eds., 9.sup.th edition, 1996, The McGraw-Hill Companies, pp. 617-631 & 1059-1062.
Grisham, M.B. et al., *Dig. Dis Sci.* 37(9): 1383-1389 (1992).
Grundman, M., Am.J.Clin.Nutr. 71:630S.-636S (2000).
Gwag, BJ et al., Neuroscience. 68:615-619 (1995).
Hall, E.D. et al., Free Radic.Biol.Med. 6:303-313 (1989).
Hall, E.D. et al., J. of Neurotrauma. 5:81-89 (1988).
Hall, E.D., Neurosurg.Clin.N.Am. 8:195-206 (1997).
Holmes, G.L. et al., Cleve. Clin. J. Med. 62:240-247 (1995).
Hussain, F.N. et al., *Br J. Clin Pharmacol*. 49(4): 323-330, (Apr. 2000).
Ikonomidou, C, et al., J. Neuropathol. Exp. Neurol. 55:211-224 (1996).

International Preliminary Examination Report for PCT/KR 00/00366, Aug. 23, 2002.
Jenner, and Olanow, Neurology 47:S161-S170 (1996).
Jenner, P., Pathol. Biol. (Paris.) 44:57-64 (1996).
Joo, C-K. et al, Investigative Ophthalmology & Visual Science 40:713-720 (1999).
Kass, I.S. et al., Exp. Neurol. 103:116-122 (1989).
Kim, E.Y. et al, European Journal of Neuroscience, 11:327-334 (1999).
Klotz et al., *Arzneimittel-Forschung. Drug Research* 43(12): 1357-1359, (Dec. 1993).
Kogure, K. et al., *Prog. Brain Res.*, 63:237-259 (1985).
Koh, J.Y. et al., J Neurosci Methods 20:83-90 (1987).
Koh, J.Y. et al., Science 234:73-76 (1986).
Koh, J.Y. et al., Science 272: 1013-1016 (1996).
Kumamoto, T. et al., *Jpn. J. Pharmacol*. 75: 187-189, 1997.
Lakowski, B. et al., Science 272: 1010-1013 (1996).
Lange, K.W. et al., Naunyn Schmiedebergs Arch.Pharmacol. 348(6):586-592 (1993).
Lee et al., *Proc. Natl. Acad. Sci.*, U.S.A. 99:7705-7710 (2002).
Lee, J-M et al., Nature 399:A7-A14 (1999).
Love, S., Brain Pathol. 9:119-131 (1999).
Marin, C. et al., Brain Res. 736:202-205 (1996).
McNamara, J.O. et al., Neuropharmacology 27:563-568 (1988).
Merello, M. et al., Clin. Neuropharmacol. 22:273-276 (1999).
Metman, L.V. et al., Neurology 51:203-206 (1998).
Minta, A. et al., Journal of biological Chemistry 264(14):8171-8178 (1989).
Montastruc, J.L. et al, Neuroscience and Biobehavioral Reviews 21(4):477-480 (1997).
Mysyk, D. D. et al., "Chloromethylation of 4-arenesulfonyl-N-methylamidoanisoles," Soviet Progress in Chemistry. 33(2), 59-62 (1967).
Nussbaumer, P. et al., "Novel Antiproliferative Agents Derived from Lavendustin A," J. Med. Chem. 37(24), 4079-84 (1994).
Okiyama, K. et al., J. Neurotrauma. 14:211-222 (1997).
Olney et al., *Science*, 244:1360-1362 (1989).
Olney, J. W. and Ho, O. L., *Nature*, 227(258): 609-611 (1970).
Olney, J. W. and Sharpe, L. G., *Science*, 166:386-388 (1969).
Olney, J. W. *Int. Rev. Neurobiol.*, 27:337-362 (1985).
Papa, S.M. et al., Ann. Neurol. 39:574-578 (1996).
Park, C,K, et al., Ann Neurol. 24:543-551 (1988).
PCT International Search Report, PCT/KR00-00366.
Prasad, K.N. et al., J. Am. Coll. Nutr. 18:413-423 (1999).
Rizzi, E. et al., "Electron Impact Spectrometry of some 5-aminosalicylic acid derivatives," Rapid Commun. Mass Spectrom. 1994, 8(2), 158-62.
Rosen, D.R. et al., Nature 362:59-62 (1993).
Rothstein, J.D. et al., Clin. Neurosci. 3:348-359 (1995).
Schapira, A. H., *Curr. Opin. Neurol.*, 9(4)260-264 (1996).
Schröder, H. et al., Clin. Pharmacol. Ther. 13:539-551 (1972).
Schubert, D. et al., *Proc. Natl. Acad. Sci.*, U.S.A. 92(6):1989-1993 (1995).
Shaw, P. J. and Ince, P. G., *J. Neurol.*, 244 Suppl 2:S3-14 (1997).
Sheardown, M. J. et al, *Science*, 247:571-574 (1990).
Siegel G. J. et al., *Basic Neurochemistry*, 6th edition, Lippincott Williams & Wilkins, 315-333 (1999).
Siesjö, B.K. et al., Eur. J. Anaesthesiol. 13:247-268 (1996).
Simon, R.P. et al., Science 226:850-852 (1984).
Sinz, E.H. et al, J of Cerebral Blood Flow and Metabolism 18:610-615 (1998).
Smith, M.A., et al., Proc. Natl. Acad. Sci. U.S.A. 94:9866-9868 (1997).
Smith, P.R. et al., Gut 20:802-805 (1979).
Sofic, E. et al., *J. Neural Transm.*, 74:199-205 (1988).
Spector, R. et al., *J. Pharmacol. Exp. Ther*. 188: 55-65 (1974).
Stenson, W.F. et al., J. Clin. Invest. 69, 494-497 (1982).
Suh, S.W. et al., Brain Res. 852 258-273 (2000).
Suh, S.W. et al., Brain Res. 852:274-278 (2000).
Wahl, C. et al., J. Clin.Invest. 101:1163-1174 (1998).
Webster's II, New Riverside University Dictionary, Riverside Publishing Company, p. 933, 1988.
Weiss et al., *Trend Pharmacol., Sci.* 21:395-401 (2001).

Weiss, J. et al., Brain Res. 380:186-190 (1986).
Weiss, J.H. et al., Neuron. 10:43-49 (1993).
Wieloch, T., Science 230:681-683 (1985).
Won, S.J. et al., Neurobiology of Disease 7:251-2599 (2000).
Wong, B.Y. et al., Neurosci.Lett. 85:261-266 (1988).
Zeidman, S.M. et al., J. Spinal. Disord. 9:367-380 (1996).

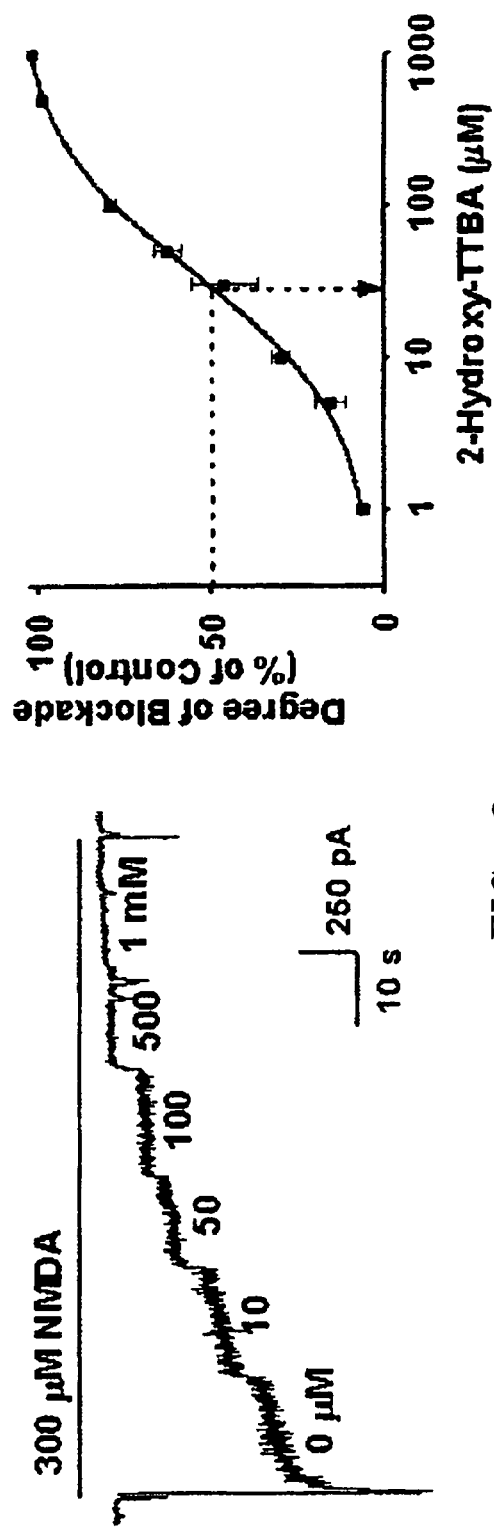
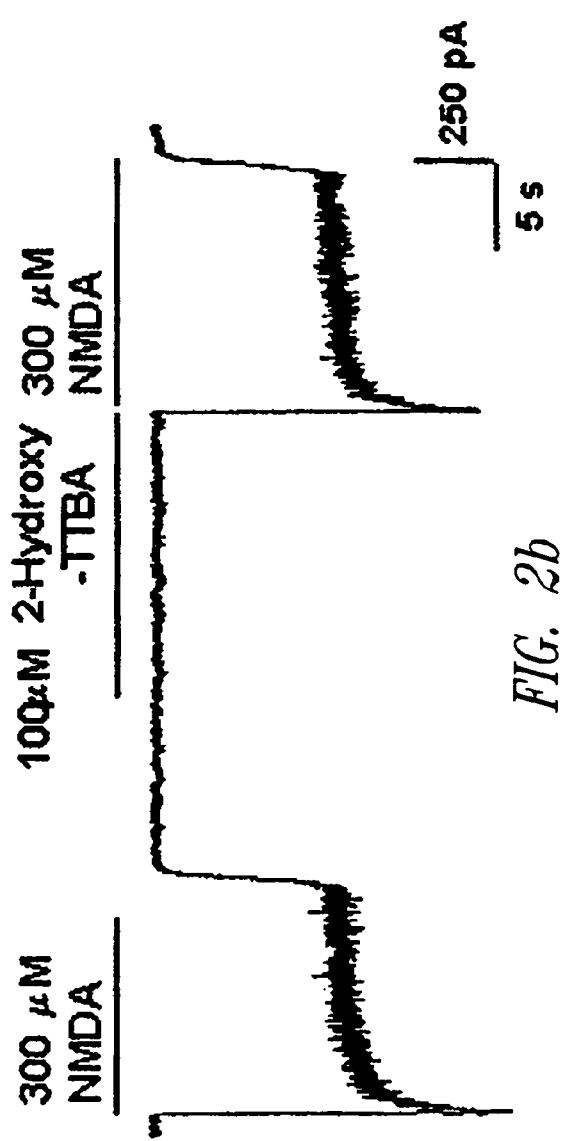
FIG. 2a
FIG. 2b

TETRAFLUOROBENZYL DERIVATIVES AND PHARMACEUTICAL COMPOSITION FOR PREVENTING AND TREATING ACUTE AND CHRONIC NEURODEGENERATIVE DISEASES IN CENTRAL NERVOUS SYSTEM CONTAINING THE SAME

This application is a divisional of U.S. patent application Ser. No. 11/165,293, filed Jun. 22, 2005, now U.S. Pat. No. 7,189,878; which application is a divisional of U.S. patent application Ser. No. 10/481,648, filed Dec. 22, 2003 and issued as U.S. Pat. No. 6,927,303; which application is a 371 of PCT/KR03/01205 filed Jun. 19, 2003; which application claims priority to Korea Application No. 10-2002-34259, filed Jun. 19, 2002; which applications are incorporated by reference herein in their entirety.

TECHNICAL FIELD

The present invention relates to a tetrafluorobenzyl derivative and a pharmaceutical composition comprising the same as a pharmaceutically effective ingredient and, more particularly, to a novel tetrafluorobenzyl derivative therapeutically effective for the treatment and prevention of neurological diseases and ocular diseases.

BACKGROUND ART

Recent advances in medicine have extended the life span of human beings and as a result, age-related acute and chronic neurological diseases, such as Alzheimer's disease, stroke, Parkinson's disease etc. increase. These neurological diseases are characterized by the progress of degeneration of specific neurons over the course of diseases. As mature neurons do not regenerate once they die, neuronal death in neurological diseases above can result in incurable loss of essential brain function including cognition, sensation, and movement and thus economic and social overload.

Exicitotoxicity, oxidative stress, and apoptosis have been implicated as major routes of neuronal death occurring in various neurological diseases and propagate through distinctive signaling pathways for each route.

Glutamate is the excitatory neurotransmitter mediating slow excitatory synaptic transmission through N-methyl-D-aspartate (NMDA) receptors and fast excitatory synaptic transmission through kainate or α-amino-3-hydroxy-5-methyl-4-isoxazolepropionic (AMPA) receptors. In the resting state of neurons, $Mg^{2+}$ blocks NMDA receptor channels in a voltage-dependent manner. With stimuli causing membrane depolarization, $Mg^{2+}$ is liberated from the NMDA channels, rendering the channels permeable to $Ca^{2+}$ and $Na^+$. Activation of NMDA receptors plays an important role in physiological process including learning and memory [Siegel G. J. et al., Basic Neurochemistry, $6^{th}$ edition, Lippincott Williams & Wilkins, 315-333 (1999)]. Besides physiological roles, brief and excess activation of NMDA receptors can cause rapidly evolving neuronal death and mechanisms underlying NMDA receptor-mediated neurotoxicity have been extensively studied over the last tow decades.

In 1969, Olney et al. reported that oral administration of monodium glutamate produced neuronal cell death in brain of mice or monkey [Olney, J. W. and Sharpe, L. G., Science, 166:386-388(1969); Olney, J. W. and Ho, O. L., Nature, 227(258): 609-611(1970)], suggesting that glutamate, the excitatory neurotransmitter, mediates neuronal excitability and death in epilepsy [Olney. J. W., Int. Rev. Neurobiol., 27:337-62:337-362(1985)]. Administration of glutamate induces neuronal death in cultured cortical neurons, which occurs through activation of NDMA receptors and depends upon $Ca^{2+}$ entry [Choi, D. W., J. Neurosci., 7(2)369-379 (1987)]. Glutamate neurotoxicity (or excitotoxicity) has been proposed as a main pathway to neuronal death in stroke as well as epilepsy [Choi. D. W., Neuron, 1:623-634(1988)]. Interrupted blood supply to brain results in deprivation of oxygen and glucose, which causes energy (ATP) failure, dysfunction of ATP-dependent ion channels, and membrane depolarization that increases glutamate release. Energy failure also reduces glutamate uptake into glial cells. Consequently, glutamate is abnormally accumulated in the synaptic cleft [Choi, D. W. and Rothman, S. M., Annu. Rev. Neurosci., 13:171-182(1990); Benveniste, H et al., J. Neurochem., 43(5):1369-1374(1984)]. The excess accumulation of glutamate causes neuronal cell death primarily through activation of NMDA receptors. In fact, administration of NMDA receptor antagonists have been reported to reduce neuronal death following hypoxic-ischemic brain injury [Goldberg, M. P. et al., J. Pharmac. Exp. Ther., 243:784-791(1987); Simon et al., Science 226:850-852 (1984); Sheardown, M. J. et al., Science 247:571-574(1990)].

Extensive evidence supports that excitotoxicity also contributes to neuronal death in neurodegenerative diseases. The key pathological features of Huntington's disease (HD) include degeneration of GABAergic neurons and selective sparing of NADPH diaphorase-containing neurons in the striatal area. These pathological features of HD are observed following the intrastriatal injections of NMDA or quinolinic acid, an NMDA receptor agonist [Ferrante, R. J et al., Science, 230(4625):561-563(1985); Beal, M. F. et al., Nature, 321(6066):168-171(1986); Koh, J. Y. et al., Science, 234(4772):73-76(1986)]. Amytrophic lateral sclerosis (ALS) is accompanied by degeneration of upper and lower motor neurons and marked by neurogenic atrophy, weakness, and fasciculation. While the pathogenesis of ALS remains to be resolved, excitotoxicity has been expected to participate in the process of the ALS. In particular, ALS patients show defects in synthesis and transport of glutamate and increased levels of extracellular glutamate [Rothstein, J. D., Clin. Neurosci., 3(6):348-359(1995); Shaw, P. J. and Ince, P. G., J. Neurol., 244 Suppl 2:S3-14(1997)].

Although NMDA receptor-mediated excitotoxicity plays a causative role in stroke and neurodegenerative diseases, the therapeutic potential of NDMA receptor antagonists has been limited by unexpected side effects in brain. In particular, systemic administration of NMDA receptor antagonists impairs normal brain function and can cause widespread neuronal damage in adult rat brain [Olney et al., Science 244:1360-1362 (1989)]. The neuropsychopathological side effects are produced by high-affinity NMDA receptor antagonists such as phencyclidine and related NMDA receptor antagosints such as MK-801 (dizocilpine maltate), tiletamine and ketamine and may be overcome with administration of channel-blocking NMDA receptor antagonists with low affinity and rapid-kinetic response [Rogawski, Amino Acids 19:133-149 (2000)].

Free radicals mediate neuronal death occurring in neurological diseases as well as tissue damage occurring in the whole body [Halliwell, B. and Gutteridge, J. M., Mol. Aspects. Med., 8(2):89-193(1985); Siesjo, B. K. et al., Cerebrovasc. Brain weight, and degrees of illness of patients etc. for the treatment of neurodegeneration.

The tetrafluorobenzyl derivatives related to the present invention may be synthesized from the following reaction schemes. However, the compounds described in the schemes are just representative of the present invention, which could include more compounds.

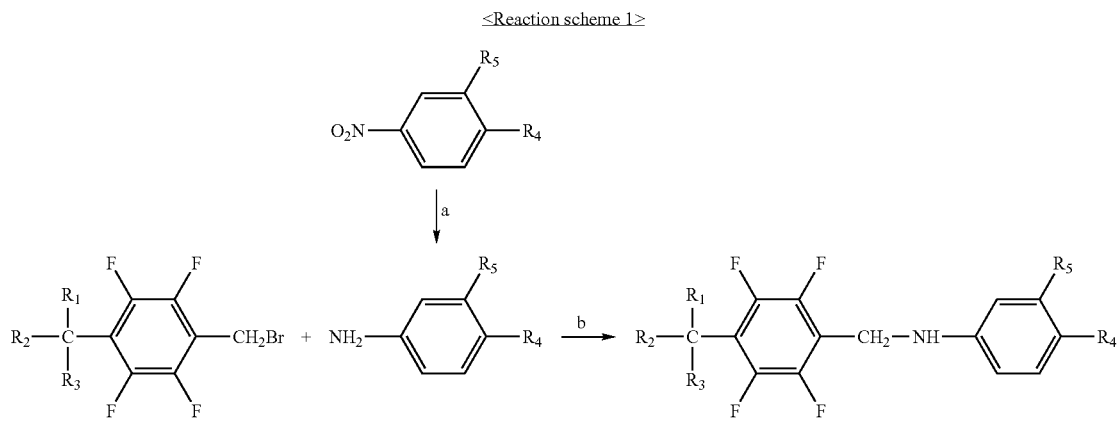

The tetrafluorobenzyl derivatives were synthesized from the following reaction. First, the nitrobenzene compounds, where hydrogens at 3 and 4 positions were substituted with $R_5$ and $R_4$ respectively, were hydrogenated for 12 hours under 3 atm pressure (reaction condition a). The resulting aniline compounds were reacted with 2,3,5,6-tetrafluoro-4-methylbenzyl bromide in DMF in the presence of *Metab. Rev.*, 1(3):165-211(1989); Schapira, A. H., *Curr. Opin. Neurol.*, 9(4)260-264(1996)]. Free radicals are produced in degenerating brain areas following hypoxic-ischemia or traumatic brain and spinal cord injuries. Antioxidants or maneuvers scavenging free radicals attenuate brain damages by hypoxic-ischemia or traumatic injuries [Flamm, E. S. et al., *Stroke*, 9(5):445-447(1978); Kogure, K. et al., *Prog. Brain Res.*, 63:237-259(1985); Chan, P. H. *J. Neurotrauma.*, 9 Suppl 2:S417-423(1992); Faden, *Pharmacol. Toxicol.* 78:12-17 (1996)]. Extensive evidence supports that free radicals are produced in brain areas undergoing degeneration in neurodegenerative diseases possibly due to point mutations in Cu/Zn superoxide dismutase in ALS [Rosen et al., *Nature* 362:59-62 (1993)], the decrease of reduced glutathione, glutathione peroxidase, and catalase, and the increase of iron in substatia nigra in Parkinson's disease [Sofic, E. et al., *J. Neural Transm.*, 74:199-205(1988); Fahn, S. and Cohen, G., Ann. *Neurol.*, 32(6):804-812(1992)], the oxidation of lipid, nucleotides, and protein, an increase of iron in degenerating neural tissues, and generation of free radicals by beta amyloid in Alzheimer's disease brain [Schubert, D. et al., *Proc. Natl. Acad. Sci. U.S.A.* 92(6):1989-1993 (1995); Richardson, J. S. et al., *Ann. N.Y. Acad. Sci.* 777: 362-367(1996)], and mitochondrial dysfunction in HD [Dexter, D. T. et al., *Ann Neurol.* 32 Suppl:S94-100(1992)]. Accordingly, antioxidants have been neuroprotective against such neurodegenerative diseases [Jenner, *Pathol. Biol.* (*Paris.*) 44:57-64 (1996); Beal, *Ann. Neurol.* 38:357-366 (1995)].

Zinc ($Zn^{2+}$) is a transition metal which is highly present and plays a dynamic role in brain. Within cells, zinc is associated with metalloproteins to control the enzymatic activity and structural stability of the proteins. Also, zinc regulates gene expression by binding to various transcription factors. In the CNS, zinc is localized at the synaptic terminal of glutamatergic neurons, released in an activity-dependent manner, and regulates activity of various neurotransmitter receptors and ion channels.

$Zn^{2+}$ mediates neurodegenerative process observed in seizure, ischemia, trauma, and Alzheimer's disease (AD). The central administration of kainate, a seizure-inducing excitotoxin, causes the translocation of $Zn^{2+}$ into postsynaptic degenerating neurons in several forebrain areas. Translocation of zinc into adjacent neurons was also observed following ischemic and traumatic brain disease, and the blockade of its transition inhibited neuronal cell death [Frederickson, C. J. and Bush, A. I., *Biometals*.14:353-366 (2001); Weiss et al., *Trend. Pharmacol. Sci.* 21:395-401 (2001)]. Zinc has been known to enter neurons through $Ca^{2+}$ permeable NMDA and AMPA/KA receptors, voltage-gated $Ca^{2+}$ channel, or zinc transporter protein, and to induce neuronal death by the activation of NADPH oxidase generating reactive oxygen species. $Zn^{2+}$ is observed in the extracellular plaque and degenerating neurons in AD, which likely contributes to neuronal degeneration in AD [Suh et al., *Brain Res.* 852:274-278(2000); Bush et al., *Science* 265: 1464-1467 (1994); Lee et al., *Proc. Natl. acad. Sci. U.S.A.* 99:7705-7710(2002)]. Therefore, the inhibition of release and toxicity of zinc has been suggested as new strategy of prevention and treatment for Alzheimer's disease [Fredrickson and Bush, Biometals; 14:353-66(2001)].

As described above, NMDA receptor-mediated excitotoxicity, oxidative stress, and zinc can contribute to neuronal death in various acute and neurodegenerative diseases in the nervous system. Thus, efficient therapeutic drugs preventing each route of neuronal deaths should be developed to treat such catastrophic neurological diseases.

We have investigated to develop neuroprotective drugs with multiple neuroprotective effects against excitotoxicity or oxidative stress and succeeded in inventing tetrafluorobenzyl derivatives that can be applied to treat stroke, trauma, and some neurodegenerative diseases.

DISCLOSURE OF THE INVENTION

Leading to the present invention, the intensive and thorough research on the treatment of disorders in the central nervous system, conducted by the present inventors, results in the finding that novel tetrafluorobenzyl derivatives have potent neuroprotective activity against various types of neuronal death induced in cell culture and animal models of neurological diseases.

Accordingly, it is an object of the present invention to provide a novel tetrafluorobenzyl derivative.

It is another object of the present invention to provide a pharmaceutically effective composition for the treatment and prevention of neurological diseases and ocular diseases.

In one aspect of the present invention, there is provided a novel tetrafluorobenzyl derivative, represented by the following chemical formula 1,

[Chemical Formula 1]

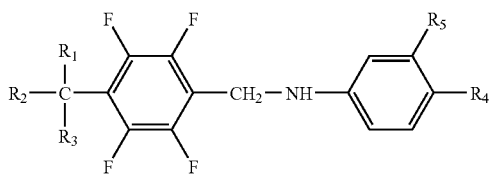

wherein, $R_1$, $R_2$, and $R_3$ are hydrogen or halogen;

$R_4$ is hydroxy, alkyl, alkoxy, halogen, alkoxy substituted with halogen, alkanoyloxy or nitro;

$R_5$ is carboxylic acid, ester of carboxylic acid substituted with $C_1$-$C_4$ alkyl, carboxyamide, sulfonic acid, halogen, or nitro;

In another aspect of the present invention, there is provided a pharmaceutical composition for the prevention and treatment of neurological diseases and ocular diseases, comprising the tetrafluorobenzyl derivative or its pharmaceutically acceptable salt as an effective ingredient.

The present invention provides a novel tetrafluorobenzyl derivative represented by the following chemical formula 1, or its pharmaceutically acceptable salt.

[Chemical Formula 1]

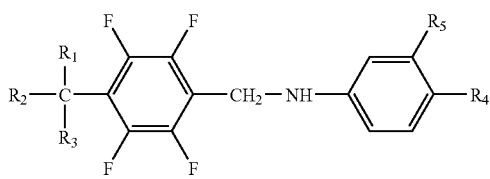

wherein, $R_1$, $R_2$, and $R_3$ are hydrogen or halogen $R_4$ is hydroxy, alkyl, alkoxy, halogen, alkoxy substituted with halogen, alkanoyloxy or nitro;

$R_5$ is carboxylic acid, ester of carboxylic acid substituted with $C_1$-$C_4$ alkyl, carboxyamide, sulfonic acid, halogen, or nitro;

In here, alkyl group is $C_1$-$C_4$ alkyl and more preferably $C_1$-$C_2$ alkyl. Alkyl described above definitely contains methyl, ethyl, propyl, isopropyl, n-butyl, sec-butyl, or tert-butyl.

Alkoxy group is $C_1$-$C_4$ and more preferably $C_1$-$C_2$ alkoxy. Alkoxy described above definitely contains methoxy, ethoxy, or propanoxy.

Halogen can be substituted with fluoride, chloride, bromide, or iodide.

Alkanoyloxy is $C_2$-$C_{10}$ alkanoyloxy and more preferably $C_3$-$C_5$ alkanoyloxy. Alkanoyloxy described above definitely contains ethanoyloxy, propanoyloxy, or cyclohexanecarbonyloxy.

In ester of carboxylic acid, carbon can be substituted with methyl, ethyl, isopropyl, or butyl.

Specific compounds of interest within Formula I are as follows:

2-Hydroxy-5-(2,3,5,6-tetrafluoro-4-trifluoromethyl-benzylamino)-benzoic acid (hereinafter, referred to as '2-Hydroxy-TTBA'), 2-Nitro-5-(2,3,5,6-tetrafluoro-4-trifluoromethylbenzylamino)benzoic acid, 2-Chloro-5-(2,3,5,6-tetrafluoro-4-trifluoromethylbenzylamino)benzoic acid, 2-Bromo-5-(2,3,5,6-tetrafluoro-4-trifluoromethylbenzylamino)benzoic acid, 2-Hydroxy-5-(2,3,5,6-tetrafluoro-4-methylbenzylamino)benzoic acid, 2-Methyl-5-(2,3,5,6-tetrafluoro-4-trifluoromethylbenzylamino)benzoic acid, 2-Methoxy-5-(2,3,5,6-tetrafluoro-4-trifluoromethylbenzylamino)benzoic acid, 5-(2,3,5,6-tetrafluoro-4-trifluoromethylbenzylamino)-2-trifluoromethoxy benzoic acid.

2-Nitro-4-(2,3,5,6-tetrafluoro-4-trifluoromethylbenzylamino)phenol,

2-Chloro-4-(2,3,5,6-tetrafluoro-4-trifluoromethylbenzylamino)phenol (hereinafter, referred to as '2-Chloro-TTP'), 2-Hydroxy-5-(2,3,5,6-tetrafluoro-4-trifluoromethylbenzylamino)Benz amide (hereinafter, referred to as '2-Hydroxy-TTA'), 2-Hydroxy-5-(2,3,5,6-tetrafluoro-4-trifluoromethylbenzylamino)benzene sulfonic acid (hereinafter, referred to as '2-Hydroxy-TTS'), Methyl 2-hydroxy-5-(2,3,5,6-tetrafluoro-4-trifluoromethylbenzylamino)benzoate, 2-Ethanoyloxy-5-(2,3,5,6-tetrafluoro-4-trifluoromethylbenzylamino)benzoic acid (hereinafter, referred to as '2-Ethan-TTBA'), 2-Propanoyloxy-5-(2,3,5,6-tetrafluoro-4-trifluoromethylbenzylamino)benzoic acid (hereinafter, referred to as '2-Propan-TTBA'), or 2-Cyclohexanecarbonyloxy-5-(2,3,5,6-tetrafluoro-4-trifluoromethylbenzylamino)benzoic acid (hereinafter, referred to as '2-Cyclohexan-TTBA').

However, the compounds described above are just representative of the present invention, which could include more compounds.

The present invention provides tetrafluorobenzyl derivatives represented by formula (I) and pharmaceutical composition for prevention and treatment of neurological and ocular diseases containing the effective component as a pharmaceutically acceptable salt.

As drugs for pharmaceutical use, the salt of the compound of formula (I) doesn't have toxicity, and should be pharmaceutically acceptable. Various kinds of salts can be used to prepare pharmaceutically acceptable salts, including non-toxic compound of the present invention.

The pharmaceutically acceptable salts of the compounds in the present invention include alkali metals, such as lithium, sodium or potassium, and alkaline earth metals, such as calcium or magnesium. Acid addition salts may be prepared by reacting the solution of pharmaceutically acceptable nontoxic salts such as hydrochloric acid, fumaric acid, maleic acid, succinic acid, acetic acid, citric acid, tartaric acid, carbonic acid, or phosphoric acid with the compound of the invention.

The compound of formula (I) in the present invention can be used for cure of normal and pathological neurodegenerative diseases among diseases or symptoms in cerebrovascular and neurological systems. In the concrete, the compound above represented by formula (I) is used for prevention or treatment of thromboembolism, ischemic stroke, hemorrhagic stroke, cerebrovascular convulsion, brain aging, traumatic brain injury, traumatic spinal cord injury, cardiac arrest, arterial hypotention, hypoglycemia, anoxia, and hypoxia. Also, the compound of formula (I) in the present invention can be beneficially used for decreasing neurodegenerative diseases such as Huntington's disease, Alzheimer's disease, senile dementia, Pick's disease, Korsakov's syndrome, olivopontocerebellar degeneration, amyotrophic lateral sclerosis (ALS), Parkinson's disease, Down's syndrome, Glutaric acidaemia, epilepsy, multi-infarct dementia, and brain inflammation. They have application to treatment of ocular diseases such as glaucoma, macular degeneration, diabetic retinopathy, uveitis. Moreover, they have application to the prevention and treatment of drug addiction, depression, and pain.

The composition of the present invention can be treated by oral administration, intravenous injection or non-oral administration, and treated by various forms such as tablet, capsule, powder, grain, sterilized solution, suspension or suppository for rectal administration. Major effective elements of the composition can be made as a solid tablet using pharmaceutical carriers, for example common tablet element such as corn dextrin, lactose, sucrose, sorbitol, talc, stearic acid, magnesium stearate, decalcium phosphate or gums, and additional pharmaceutical diluted solution. Tablets or pellets of the pharmaceutical composition in the present invention can be manufactured for sustained release dosage form as facilitated forms for administration using well-known coating method etc. in the appropriate industry. For example, tablets or pellets can be composed with inner and outer administrative elements. The inner administrative elements of tablets or pellets can be manufactured as wrapped with outer administrative elements. Liquid forms of the composition in the present invention manufactured for oral administration or the injection include solution, appropriately flavored syrup, water-soluble suspension, water-insoluble suspension, emulsion made by edible oil such as cotton oil, sesame oil, coconut oil, or peanut oil, elixir, and similar pharmaceutical carriers. Tragacanth gum, acacia, alginic acid sodium salt, dextran, sodium carboxymethylcellulose, methylcellulose, polyvinylpyrrolidone, or synthesized or natural gums like gelatin etc can be used as appropriated aid to dispersion or suspension in making water-soluble suspension.

Quantity of medication can be determined by several related factors such as diseases, age, sex, triethylamine for 12 hours to give the desired tetrafluorobenzyl derivatives (reaction condition b).

In the above scheme, $R_1$, $R_2$, and $R_3$ represent hydrogen or halogen; $R_4$ represents hydroxy, alkyl, alkoxy, halogen, alkoxy substituted with halogen, alkanoyloxy, nitro; $R_5$ represents carboxylic acid, esters of carboxylic acid, carboxyamide, sulfonic acid, halogen, and nitro group.

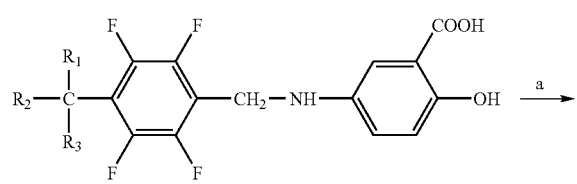

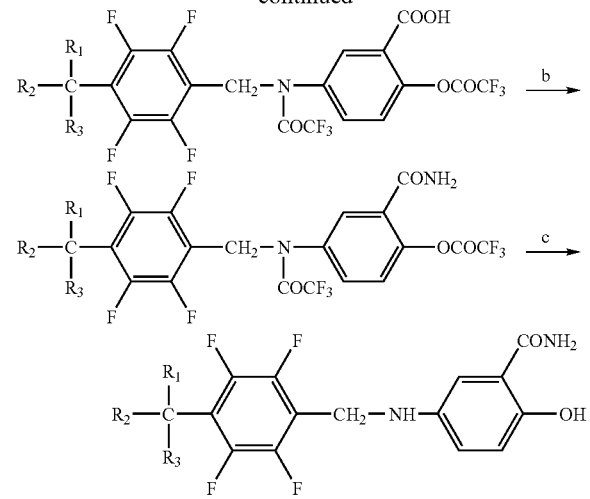

For the synthesis of compound where $R_4$ is hydroxy group and $R_5$ is carboxyamide group, the hydroxy and amino group in 5-(2,3,5,6-tetrafluoro-4-trifluorobenzylamino)benzoic acid were first protected with trifluoro group by reacting with trifluoromethyl acetic anhydride in the catalytic amount of c-$H_2SO_4$ (reaction condition a). The resulting 2-carboxy-5-[2,3,5,6-tetrafluoro-4-trifluoromethyl-benzyl]-(2,2,2-trifluoroacetyl)amino]phenyl ester compound was then reacted with $SOCl_2$ followed by ammonium carbonate to give 2-carbamoyl-4-[2,3,5,6-tetrafluoro-4-trifluoromethyl-benzyl-(2,2,2-trifluoroacetyl)amino]phenyl ester compound (reaction condition b), which was then hydrolyzed with HCl solution to give the desired carboxyamide compound. (reaction condition c) In this scheme, $R_1$, $R_2$, $R_3$ and $R_4$ are same groups, which are previously defined while $R_5$ are $C_1$-$C_4$ substituted alkyl group.

SYNTHESIS EXAMPLE 1

Preparation of 2-hydroxy-5-(2,3,5,6-tetrafluoro-4-trifluoromethylbenzylamino)benzoic acid (2-Hydroxy-TTBA)

To a solution of 5-aminosalicylic acid (1.02 g, 6.66 mmole, purchased from Aldrich Chemical Company, USA, A7, 980-9) and triethylamine (1 ml) in dried DMF (80 ml) was added 2,3,5,6-tetrafluoro-4-trifloromethylbenzyl bromide (1.23 g, 7.18 mmole)(Aldrich, 40, 640-6) at room temperature under a nitrogen atmosphere. The reaction mixture was stirred for 2 hr at room temperature and then solvent was removed in vacuo. The reaction mixture was diluted with ethyl acetate and then extracted with ethyl acetate. The organic layer was washed with water and brine, and then dried over anhydrous $MgSO_4$. After evaporation of the solvent, the residue was recrystallized from ether/hexane (1:10) to give 1.60 g (64% yield) of 2-hydroxy-5-(2,3,5,6-tetrafluoro-4-trifluoromethylbenzylamino)benzoic acid as a white solid.

mp 179° C., $^1$H-NMR: 8.0 (s, 1H), 7.3 (d, 1H), 6.7 (t, 1H), 5.5 (s, 2H), IR(KBr pellet): 3386, 1741, 1500 cm$^{-1}$

| Elemental analysis for $C_{15}H_8F_7NO_3$ | | | | | |
|---|---|---|---|---|---|
| | % C | % H | % N | % F | % O |
| Calculated | 47.01 | 2.10 | 3.66 | 34.70 | 12.53 |
| Found | 47.00 | 2.03 | 3.69 | | |

SYNTHESIS EXAMPLE 2

Preparation of 2-nitro-5-(2,3,5,6-tetrafluoro-4-trifluoromethybenzylamino)benzoic acid According to the similar procedure in Synthesis Example 1, by using 5-amino-2-nitrobenzoic acid (1.03 g, 5.65 mmole) and 2,3,5,6-tetrafluoro-4-trifloromethylbenzyl bromide (1.01 g, 6.04 mmole)(ACROS, 33074-0010), 1.50 g (76.3% yield) of 2-nitro-5-(2,3,5,6-tetrafluoro-4-trifluoromethylbenzylamino)benzoic acid was obtained as a pale yellow solid.

mp 121° C., $^1$H-NMR: 8.0 (d, 1H), 7.3 (s, 1H), 6.7 (d, 1H), 5.5 (s, 2H),

IR(KBr pellet) 3417, 1703, 1504 cm$^{-1}$

| Elemental analysis for $C_{15}H_7F_7N_2O_4$ | | | | | |
|---|---|---|---|---|---|
| | % C | % H | % N | % F | % O |
| Calculated | 43.71 | 1.71 | 6.80 | 32.36 | 15.53 |
| Found | 43.37 | 1.68 | 6.50 | | |

SYNTHESIS EXAMPLE 3

Preparation of 2-chloro-5-(2,3,5,6-tetrafluoro-4-trifluoromethylbenzylamino)benzoic acid According to the similar procedure in Synthesis Example 1, by using 5-amino-2-chlorobenzoic acid (1.02 g, 5.94 mmole)(ACROS, 32525-5000), DMF: (50 ml) and 2,3,5,6-tetrafluoro-4-trifloromethylbenzyl bromide (1.16 g, 6.99 mmole), 2.04 g (85.5% yield) of 2-chloro-5-(2,3,5,6-tetrafluoro-4-trifluoromethylbenzylamino) benzoic acid was obtained as a pale brown solid.

mp 58° C., $^1$H-NMR: 7.26 (d, 1H), 7.24 (s, 1H), 6.7 (d, 1H), 4.12 (s, 2H),

IR(KBr pellet): 3402, 1720, 1494, 1434, 929 cm$^{-1}$

HPLC (0.01% TFA-ethyl acetate: 0.1 TFA-water=80:20, Rt=4.2 mins): 97% purity

| Elemental analysis for $C_{15}H_7ClF_7NO_4$ | | | | | |
|---|---|---|---|---|---|
| | % C | % H | % N | % F | % O |
| Calculated | 44.85 | 1.76 | 3.49 | 33.11 | 7.97 |
| Found | 44.83 | 2.31 | 3.43 | | |

SYNTHESIS EXAMPLE 4

Preparation of 2-bromo-5-(2,3,5,6-tetrafluoro-4-trifluoromethylbenzylamino)benzoic acid (4-1) Preparation of 5-amino-2-bromobenzoic acid A mixture of 2-bromo-5-nitrobenzoic acid (1.10 g, 4.06 mmol)(Aldrich, 38, 184-5), activated Pd—C (43.62 mg, 0.41 mmol) (Aldrich, 20, 569-9) in methanol (30 ml) was hydrogenated for 4 hr under 30 psi of hydrogen pressure. After the mixture was filtered, the filtrate was concentrated to give 0.80 g (91.2% yield) of 5-amino-2-bromobenzoic acid as a pale yellow solid.

IR(KBr pellet): 3111; 2558, 2499, 1716, 1676 cm$^{-1}$ (4-2) Preparation of 2-bromo-5-(2,3,5,6-tetrafluoro-4-trifluoromethylbenzylamino)benzoic acid According to the similar procedure in Synthesis Example 1, by using 5-amino-2-bromobenzoic acid (1.05 g, 6.12 mmole) which was prepared from Synthesis Example (4-1), DMF (50 ml) and 2,3,5,6-tetrafluoro-4-trifloromethylbenzyl bromide (1.16 g, 6.99 mmole), 2.02 g (76.9% yield) of 2-bromo-5-(2,3,5,6-tetrafluoro-4-trifluoromethylbenzylamino)benzoic acid was obtained as a pale yellow solid.

mp 70° C., $^1$H-NMR: 7.42 (d, 1H), 7.3 (s, 1H), 6.9 (d, 1H), 5.5 (s, 2H),

IR(KBr pellet) 3438, 1695, 1491, 1425, 939 cm$^{-1}$

HPLC (0.1% TFA-ethyl acetate: 0.1% TFA-water=80:20, Rt=4.5 mins) 99% purity

| Elemental analysis for $C_{15}H_7BrF_7NO_2$ | | | | | | |
|---|---|---|---|---|---|---|
| | % C | % H | % N | % Br | % F | % O |
| Calculated | 40.38 | 1.58 | 3.14 | 17.91 | 29.81 | 7.17 |
| Found | 44.62 | 1.57 | 3.79 | | | |

SYNTHESIS EXAMPLE 5

Preparation of 2-hydroxy-5-(2,3,5,6-tetrafluoro-4-methylbenzylamino)benzoic acid According to the similar procedure in Synthesis Example 1, by using 4-methyl-2,3,5,6-tetrafluoro-benzyl bromide (1.23 g, 7.18 mmole) (Aldrich, 40, 646-6)instead of 2,3,5, 6-tetrafluoro-4-trifluoromethyl benzylbromide, 1.60 g (64.0% yield) of 2-hydroxy-5-(2,3,5,6-tetrafluoro-4-methylbenzylamino)benzoic acid was obtained as a white solid.

mp 212° C., $^1$H-NMR: 8.0 (s, 1H), 7.3 (d, 1H), 6.7 (t, 1H), 5.5 (s, 2H), 2.2~2.3 (s, 3H),

IR(KBr pellet): 3386, 1741, 1500 cm$^{-1}$

| Elemental analysis for $C_{15}H_{11}F_4NO_3$ | | | | | |
|---|---|---|---|---|---|
| | % C | % H | % N | % F | % O |
| Calculated | 54.72 | 3.37 | 4.25 | 23.08 | 14.58 |
| Found | 54.90 | 3.60 | 4.06 | | |

SYNTHESIS EXAMPLE 6

Preparation of 2-methyl-5-(2,3,5,6-tetrafluoro-4-trifluoromethylbenzylamino)benzoic acid (6-1) Preparation of 2-methyl-5-nitrobenzoic acid To a solution of 2-methylbenzoic acid (3.05 g, 22.3 mmole) (ACROS, 13904-0010) in c-HNO$_3$ (20 ml) was carefully added Conc.H$_2$SO$_4$ (15 ml) at 0° C. The resulting solution was refluxed at 100-120° C. for 5 hours. After the reaction mixture was cooled to room temperature, 50 ml of ice chip was added. The resulting precipitate was filtered, washed with water and dried to give 3.90 g (97.5% yield) of 2-methyl-5-nitrobenzoic acid as a white solid.

IR(KBr pellet): 1531, 1350 cm$^{-1}$ (6-2) Preparation of 5-Amino-2-methylbenzoic acid.

According to the similar procedure in Synthesis Example (4-1), by using 2-methyl-5-nitrobenzoic acid (4.10 g, 22.6 mmole) which was prepared from Synthesis Example (6-1), 2.01 g (60.0% yield) of 5-amino-2-methylbenzoic acid was obtained as a white solid.

IR(KBr pellet): 3437, 3336, 1633, 1400 cm$^{-1}$ (6-3) Preparation of 2-methyl-5-(2,3,5,6-tetrafluoro-4-trifluoromethylbenzylamino)benzoic acid According to the similar procedure in Synthesis Example 1, by using 5-amino-2-methylbenzoic acid (2.06 g 15.0 mmole), DMF (60 ml), TEA (4 ml), and 2,3,5,6-tetrafluoro-4-trifluoromethylbenzyl bromide (5.52 ml, 17.7 mmole), 1.50 g (27.0% yield) of 2-methyl-5-(2,3,5,6-tetrafluoro-4-trifluoromethylbenzylamino)benzoic acid was obtained as a yellow solid.

mp 84° C.,

1H-NMR: 7.32(s, 1H), 7.3(d, 1H), 6.9(d, 1H), 5.5(s, 2H), 2.2(s, 3H),

IR(KBr pellet): 3417, 1716, 1496 cm$^{-1}$

| Elemental analysis for $C_{16}H_{10}F_7NO_2$ | | | | |
|---|---|---|---|---|
| % C | % H | % N | % F | % O |
| Calculated 50.41 | 2.64 | 3.53 | 33.48 | 12.08 |
| Found 50.40 | 2.60 | 3.39 | | |

SYNTHESIS EXAMPLE 7

Preparation of 2-methoxy-5-(2,3,5,6-tetrafluoro-4-trifluoromethylbenzylamino)benzoic acid (7-1) Preparation of 2-methoxy-5-nitrobenzoic acid According to the similar procedure in Synthesis Example (6-1), by using 2-methoxybenzoic acid (2.10 g, 13.79 mmole) (ACROS, 17375-2000), 2.50 g (97.0% yield) of 2-methoxy-5-nitrobenzoic acid was obtained as a white solid.

IR(KBr pellet): 3099, 2986, 2965, 1736, 1547 cm$^{-1}$ (7-2) Preparation of 5-amino-2-methoxy-benzoic acid According to the similar procedure in Synthesis Example (4-1), by using 2-methoxy-5-nitrobenzoic acid (4.10 g, 22.6 mmole) which was prepared from Synthesis Example (7-1), 1.90 g (98.0% yield) of 5-amino-2-methoxybenzoic acid was obtained as a brown solid.

IR(KBr pellet): 1394, 1220 cm$^{-1}$ (7-3) Preparation of 2-methoxy-5-(2,3,5,6-tetrafluoro-4-trifluoromethylbenzylamino)benzoic acid According to the similar procedure in Synthesis Example 1, by using 5-amino-2-methoxy-benzoic acid (2.10 g, 12.7 mmole), DMF (50 ml), TEA (6 ml), and 2,3,5,6-tetrafluoro-4-trifluoromethylbenzyl bromide (2.00 ml, 14.0 mmole), 1.50 g (31.5% yield) of 2-methoxy-5-(2,3,5,6-tetrafluoro-4-trifluoromethylbenzylamino)benzoic acid was obtained as a yellow solid:

mp 94° C., $^1$H-NMR 7.42(s, 1H), 6.4(d, 1H), 6.2(d, 1H), 5.5(s, 2H), 3.73(s, 3H),

IR(KBr pellet): 3429, 1730, 1496 cm$^{-1}$

| Elemental analysis for $C_{16}H_{10}F_7NO_3$ | | | | |
|---|---|---|---|---|
| % C | % H | % N | % F | % O |
| Calculated 48.38 | 2.54 | 3.53 | 33.48 | 12.08 |
| Found 47.50 | 2.20 | 3.39 | | |

SYNTHESIS EXAMPLE 8

Preparation of 5-(2,3,5,6-tetrafluoro-4-trifluoromethyl-benzylamino)-2-trifluoromethoxybenzoic acid (8-1) Preparation of 5-nitro-2-trifluoromethoxybenzoic acid According to the similar procedure in Synthesis Example (6-1)(Lancaster, 15687), by using 2-trifluoromethoxybenzoic acid (2.10 g, 9.81 mmole), 1.40 g (55.0% yield) of 5-nitro-2-trifluoromethoxybenzoic acid was obtained as a white solid.

IR(KBr pellet): 1488, 1354 cm$^{-1}$ (8-2) Preparation of 5-amino-2-trifluoromethoxybenzoic acid According to the similar procedure in Synthesis Example (4-1), by using 5-nitro-2-trifluoromethoxybenzoic acid (1.40 g, 5.34 mmole) which was prepared from Synthesis Example (8-1), 1.02 g (90.0% yield) of 5-amino-2-trifluoromethoxybenzoic acid was obtained as a pale yellow solid.

IR(KBr pellet): 1627, 1369 cm$^{-1}$ (8-3) Preparation of 5-(2,3,5,6-tetrafluoro-4-trifluoromethylbenzylamino)-2-trifluoromethoxybenzoic acid According to the similar procedure in Synthesis Example 1, by using 5-amino-2-trifluoromethoxybenzoic acid (1.35 g, 6.23 mmole), DMF (50 ml), TEA (6 ml), and 2,3,5,6-tetrafluoro-4-trifluoromethylbenzyl bromide (1.10 ml, 6.7.3 mmole), 2.25 g (81.0% yield) of 5-(2,3,5,6-tetrafluoro-4-trifluoromethylbenzylamino)-2-trifluoromethoxybenzoic acid was obtained as a yellow solid.

mp 38° C., $^1$H-NMR 7.3 (s, 1H), 7.12 (d, 1H), 6.8 (d, 1H), 5.5 (s, 2H),

IR(KBr pellet): 3383, 1712, 1504, 1446, 929 cm$^{-1}$

| Elemental analysis for $C_{16}H_7F_{10}NO_3$ | | | | |
|---|---|---|---|---|
| % C | % H | % N | % F | % O |
| Calculated 42.59 | 1.56 | 3.0 | 42.10 | 10.64 |
| Found 41.24 | 2.20 | 3.39 | | |

SYNTHESIS EXAMPLE 9

Preparation of 2-nitro-4-(2,3,5,6-tetrafluoro-4-trifluorormethylbenzylamino)phenol According to the similar procedure in Synthesis Example 1, by using 4-amino-2-nitrophenol (1.00 g, 6.49 mmole), DMF (30 ml), TEA (0.5 ml), and 2,3,5,6-tetrafluoro-4-trifluoromethylbenzyl bromide (1.30 g, 7.78 mmole), 1.00 g (40.0% yield) of 2-nitro-4-(2,3,5,6-tetrafluoro-4-trifluoromethylbenzylamino)phenol was obtained as a reddish solid.

mp 126-128° C., $^1$H-NMR(DMSO-$d_6$) δ 4.23 (d, 2H), 6.93 (m, 2H), 7.12 (s, 1H), $^{13}$C NMR(DMSO-$d_6$) δ 36.36, 105.48, 120.63, 122.64, 123.32, 136.17, 140.86, 142.34, 144.06, 144.83, 146.44, 151.23,

IR(neat): 3391, 3255, 1545, 1339 cm$^{-1}$

Elemental analysis for $C_{14}H_7F_7N_2O_3$

|  | % C | % H | % N | % F | % O |
|---|---|---|---|---|---|
| Calculated | 43.65 | 2.09 | 7.27 | 28.46 | 13.69 |
| Found | 43.68 | 2.05 | 7.26 |  |  |

SYNTHESIS EXAMPLE 10

Preparation of 2-chloro-4-(2,3,5,6-tetrafluoro-4-trifluoromethylbenzylamino)phenol According to the similar procedure in Synthesis Example 1, by using 4-amino-2-chlorophenol (3.00 g, 19.6 mmole), DMF (80 ml), TEA (0.5 ml), and 2,3,5,6-tetrafluoro-4-trifluoromethylbenzyl bromide (1.40 g, 8.36 mmole), 2.00 g (76.0% yield) of 2-chloro-5-(2,3,5,6-tetrafluoro-4-methylbenzylamino)phenol was obtained as a yellow solid.

mp 52° C., $^1$H-NMR(CDCl$_3$) 6.9 (d, 1H), 6.7 (s, 1H), 6.5 (d, 1H), 4.4 (s, 2H),

IR(KBr pellet) 3382, 1687, 1617, 1586 cm$^{-1}$

Elemental analysis for $C_{14}H_7F_7N_2O_3$

|  | % C | % H | % N | % Cl | % F | % O |
|---|---|---|---|---|---|---|
| Calculated | 42.00 | 1.89 | 3.75 | 9.49 | 35.59 | 4.28 |
| Found | 45.23 | 1.49 | 3.74 |  |  |  |

SYNTHESIS EXAMPLE 11

Preparation of 2-hydroxy-5-(2,3,5,6-tetrafluoro-4-trifluoromethylbenzylamino)benzamide (11-1) Preparation of 2-carboxy-4-[2,3,5,6-tetrafluoro-4-trifluoromethyl-benzyl]-(2,2,2-trifluoroacetyl)amino]phenyl trifluoroacetate To a solution of 2-hydroxy-5-(2,3,5,6-tetrafluoro-4-trifluoromethylbenzylamino) benzoic acid (2.00 g, 5.12 mmole) and trifluoroactic anhydride (15 ml) was added c-H$_2$SO$_4$ (0.50 ml) at 10° C. under a nitrogen atmosphere. The reaction mixture was stirred for 20 min at room temperature and then quenched with an ice (10 g). After the solvent was removed in vacuo, the residue was dissolved in ethyl acetate (50 ml). The organic layer was washed with water (20 ml×2), 10% NaHCO$_3$ (20 ml×3), 0.5 N HCl (20 ml×2), and water (20 ml). The organic layer was dried over anhydrous Na$_2$SO$_4$. After evaporation of the solvent, the residue was recrystallized from ethyl acetate/hexane (1:10) to give 1.40 g (47% yield) of 2-carboxy-4-[2,3,5,6-tetrafluoro-4-trifluoromethylbenzyl]-(2,2,2-trifluoroacetyl) amino]phenyl trifluoroacetate as an yellow solid.

mp 174-180° C.

$^1$H-NMR(DMSO-$d_6$) δ 5.16(d, 2H), 6.94(d, 1H), 7.44(d, 1H), 7.81(s, 1H), $^{13}$C-NMR(DMSO-$d_6$) δ 43.03, 113.2, 114.3, 117.2, 117.8, 118.9, 128.7, 130.2, 135.5, 141.8, 143.8, 144.3, 146.2, 146.3, 155.2, 155.5, 161.6, 170.5,

IR(neat): 1711, 1673, 1498, 1331, 724 cm$^{-1}$ (11-2) Preparation of 2-carbamoyl-4-[2,3,5,6-tetrafluoro-4-trifluoromethylbenzyl-(2,2,2-trifluororacetyl)amino]phenyl trifluoroacetate To a solution of 2-carboxy-4-(2,3,5,6-tetrafluoro-4-trifluoromethylbenzyl-(2,2,2 trifluoroacetyl)amino) phenyl trifluoroacetate (6.00 mg, 1.05 mmole) in anhydrous methylene chloride (15 ml) was added SOCl$_2$ (1.18 ml, 21.0 mmole) at 40° C. under a nitrogen atmosphere. After the reaction mixture was stirred for 1 hr, the solvent was removed in vacuo. The resulting residue was dissolved in anhydrous methylene chloride (60 ml) and added with ammonium carbonate (assay>30%, 2.00 g). After the reaction mixture was stirred for 1 hr, it was filtered to remove the remained ammonium carbonate. The organic layer was washed with water (40 ml×3) and then dried over anhydrous Na$_2$SO$_4$. After evaporation of the solvent, the residue was recrystallized from methylene chloride/hexane (1:10) to give 370 mg (61% yield) of 2-carbamoyl-4-[2,3,5,6-tetrafluoro-4-trifluoromethyl-benzyl-(2,2,2-trifluororacetyl) amino]phenyl trifluoroacetate as a white solid.

mp 179-180° C., $^1$H-NMR(DMSO-$d_6$) δ 5.05(d, 2H), 6.91(d, 1H), 7.20(d, 1H), 7.62(s, 1H), $^{13}$C NMR(DMSO-$d_6$) δ 42.31, 114.05, 114.39, 117.25, 118.28, 118.60, 127.47, 128.43; 134.14, 141.66, 143.72, 144.20, 146.26, 155.48, 161.19, 170.32,

IR(neat) 3415, 3202, 1692, 1673, 1498, 1331 cm$^{-1}$ (11-3) Preparation of 2-hydroxy-5-(2,3,5,6-tetrafluoro-4-trifluoromethylbenzylamino) benzamide To a solution of 2-carbamoyl-4-[2,3,5,6-tetrafluoro-4-trifluoromethylbenzyl-(2,2,2-trifluororacetyl)amino]phenyl trifluoroacetate (300 mg, 0.52 mmole) in methanol (8 ml) and water (3 ml) was added c-HCl (2.0 ml) at 40° C. under a nitrogen atmosphere. After the reaction mixture was stirred for 24 hr, the organic solvent was removed in vacuo. The residue was extracted with ethyl-acetate (20 ml×3). The organic layer was washed with water and then dried over anhydrous Na$_2$SO$_4$. After evaporation of the solvent, the residue was recrystallized from methylene chloride/hexane (1:10) to give 120 mg (60% yield) of 2-hydroxy-5-(2,3,5,6-tetrafluoro-4-trifluoromethylbenzylamino)benzamide as a white solid.

mp 143-145° C., $^1$H-NMR(DMSO-$d_6$) δ 4.37(s, 2H), 6.63(d, 1H), 6.76(d, 1H), 7.14(s, 1H), $^{13}$C NMR(DMSO-$d_6$) δ 36.25, 111.20, 112.36, 117.44, 121.71, 123.29, 123.46, 139.87, 141.61, 143.55, 145.86, 146.07, 153.12, 171.56,

IR(neat) 3453, 3415, 3202, 1692, 1673, 735 cm$^{-1}$

SYNTHESIS EXAMPLE 12

Preparation of 2-hydroxy-5-(2,3,5,6-tetrafluoro-4-trifluoromethylbenzylamino)benzene sulfonic acid According to the similar procedure in Synthesis Example 1, by using 4-amino-2-hydroxybenzene sulfonic acid (1.00 g, 5.30 mmole), DMF (10 ml), TEA (1.0 ml), and 2,3,5,6-tetrafluoro-4-trifluoromethylbenzyl bromide (0.88 g, 5.30 mmole), 0.61 g (28.0% yield) of 2-hydroxy-5-(2,3,5,6-tetrafluoro-4-trifluoromethylbenzylamino)benzene sulfonic acid was obtained as a yellow solid.

mp: above 300° C.,
$^1$H-NMR(DMSO-$d_6$) δ 4.28(s, 2H), 5.58(m, 2H), 6.82(s, 1H),
$^{13}$C NMR(DMSO-$d_6$) δ 32.08, 106.41, 111.39, 112.10, 119.15, 119.33, 119.51, 126.11, 135.09, 137.17, 139.17, 139.70, 139.89, 140.40, 140.59, 141.61,
IR(neat) 3427, 3227, 1492, 1331, 1196, 1135, 628 cm$^{-1}$

SYNTHESIS EXAMPLE 13

Preparation of methyl 2-hydroxy-5-(2,3,5,6-tetrafluoro-4-trifluoromethylbenzylamino) benzoate (13-1) Preparation of methyl 5-amino-2-hydroxybenzoate To a solution of 5-aminosalicylic acid (3.00 g, 19.6 mmole) in methanol (80 ml) was added c-$H_2SO_4$ (8 ml) at 0° C. After the reaction mixture was refluxed for 6 hr, the solvent was removed in vacuo. The resulting residue was partitioned with ethyl acetate and water. The organic layer was washed with water (40 ml×3) and then dried over anhydrous $MgSO_4$. After evaporation of the solvent, the residue was recrystallized from ethyl acetate/hexane to give 2.50 g (76% yield) of methyl 5-amino-2-hydroxybenzoate as a yellow solid.

H-NMR(CDCl$_3$) δ 7.2(s, 1H), 6.7(d, 1H), 6.6(d, 1H),
IR(KBr pellet) 3406, 3327, 2950, 1672, 1616, 1492, 1440, 788 cm$^{-1}$ (13-2) Preparation of methyl 2-hydroxy-5-(2,3,5,6-tetrafluoro-4-trifluoromethylbenzylamino)benzoate According to the similar procedure in Synthesis Example 1, by using methyl 5-amino-2-hydroxybenzoate (2.00 g, 11.9 mmole), DMF (60 ml), TEA (0.5 ml), and 2,3,5,6-tetrafluoro-4-methylbenzyl bromide (2.60 g, 14.3 mmole), 3.20 g (85.0% yield) of methyl 2-hydroxy-5-(2,3,5,6-tetrafluoro-4-trifluoromethylbenzylamino)benzoate was obtained as a pale yellow solid:

mp: 127° C.,
$^1$H-NMR(CDCl$_3$) δ 7.15(s, 1H), 6.9(d, 1H), 6.7(d, 1H), 4.5(s, 2H), 3.9(s, 3H),
IR(KBr pellet) 3382, 1687, 1617, 1586 cm$^{-1}$

| Elemental analysis for $C_{16}H_{10}F_7NO_3$ | | | | | |
|---|---|---|---|---|---|
| | % C | % H | % N | % F | % O |
| Calculated | 48.38 | 2.54 | 3.53 | 33.48 | 12.08 |
| Found | 48.12 | 2.54 | 3.43 | | |

SYNTHESIS EXAMPLE 14

Preparation of 2-ethanoyloxy-5-(2,3,5,6-tetrafluoro-4-trifluoromethyl-benzylamino)benzoic acid (14-1) Preparation of 5-tert-butoxycarbonylamino-2-hydroxybenzoic acid The mixture of 5-aminosalicylic acid (1.01 g, 6.59 mmole), Di-BOC (2.87 g, 13.1 mmol), TEA (1.0 ml) in DMF (20.0 ml) was stirred for 2 hr at room temperature. After the reaction mixture was concentrated, the residue was dissolved in ethyl acetate. The organic layer was washed with water and dried over anhydrous $Na_2SO_4$. After evaporation of the solvent, the residue was recrystallized from ethyl acetate/hexane to give 1.42 g (84% yield) of 5-tert-butoxy-2-hydroxybenzoic acid as a white solid.

mp: 282° C.,
$^1$H-NMR(DMSO-$d_6$) δ7.9~8.0 (s, 1H), 7.4~7.5 (d, 1H), 6.8~6.9 (d, 1H), 1.4-1.6 (s, 9H),
$^{13}$C NMR(DMSO-$d_6$) δ171.93, 156.50, 152.97, 131.06, 126.36, 119.39, 117.03, 113.13, 79.05, 28.42

(14-2) Preparation of 2-ethanoyloxy-5-tert-butoxycarbonylaminobenzoic acid

To a solution of 5-tert-butoxycarbonylamino-2-hydroxybenzoic acid (1.02 g, 4.02 mmole) in DMF (20.0 ml) was added with acetyl chloride (39 mg, 4.83 mmole) and potassium carbonate (555 mg, 4.02 mmole). The reaction mixture was stirred for 4 hr at room temperature. After the reaction mixture was concentrated, the residue was dissolved in ethyl acetate. The organic layer was washed with water and brine and dried over anhydrous $Na_2SO_4$. After evaporation of the solvent, the residue was recrystallized from ethyl acetate/hexane to give 0.62 g (52% yield) of 2-ethanoyloxy-5-tert-butoxycarbonylaminobenzoic acid as a white solid.

mp: 76-78° C.,
$^1$H-NMR(DMSO-$d_6$) δ 7.9~8.0 (s, 1H), 7.4~7.5 (d, 1H), 6.8~6.9 (d, 1H), 2.0~2.1 (S, 3H), 1.4~1.6 (s, 9H),
$^{13}$C NMR(DMSO-$d_6$) δ 171.88, 165.59, 156.49, 144.71, 131.27, 124.06, 79.64, 28.441, 21.13.

(14-3) Preparation of 2-ethanoyloxy-5-aminobenzoic acid

The mixture of 2-ethanoyloxy-5-tert-butoxycarbonylaminobenzoic acid (1.01 g, 3.42 mmole) in TFA/$CH_2Cl_2$ (20.0 ml. 1:1 v/v) was stirred for 30 min at room temperature. After the reaction mixture was concentrated, the residue was dissolved in ether. The resulting residue was recrystallized from ethyl acetate/hexane to give 0.65 g (97% yield) of 2-ethanoyloxy-5-aminobenzoic acid as a white solid.

mp: 133-136° C.,
$^1$H-NMR(DMSO-$d_6$) δ 7.5~7.6 (s, 1H), 7.2~7.3 (d, 1H), 7.0~7.1 (d, 1H), 2.1~2.2 (s, 3H),
$^{13}$C NMR(DMSO-$d_6$) δ 170.83, 165.57, 143.40, 124.41, 123.45, 121.09, 118.64, 113.98, 30.98.

(14-4) Preparation of 2-ethanoyloxy-5-(2,3,5,6-tetrafluoro-4-trifluoromethylbenzylamino) benzoic acid According to the similar procedure in Synthesis Example 1, by using 2-ethanoyloxy-5-aminobenzoic acid (0.81 g, 4.10 mmole) which was prepared from Synthesis Example (14-3), DMF (15 ml), TEA (0.1 ml), tetrabutyl ammonium iodide (5 mg), and 2,3,5,6-tetrafluoro-4-trifluoromethylbenzyl bromide (1.02 ml, 6.15 mmole), 0.92 g (53.0% yield) of was obtained 2-ethanoyloxy-5-(2,3,5,6-tetrafluoro-4-trifluoromethylbenzylamino)benzoic acid as a white solid.

mp: 185-187° C.,
$^1$H-NMR(DMSO-$d_6$) δ 2.16(s, 3H), 4.46(s, 2H), 6.82(d, 1H), 6.88(d, 1H), 7.17(s, 1H), $^{13}$C NMR(DMSO-d$_6$) δ 21.64, 36.37, 114.36, 116.97, 123.94, 127.78, 124.81, 141.40, 142.44, 144.44, 145.04, 145.84, 146.85, 166.35, 170.18,

IR(KBr pellet) 3410, 1747, 1705, 1489 cm$^{-1}$

Elemental analysis for C$_{17}$H$_{10}$F$_7$NO$_4$

| | % C | % H | % N | % F | % O |
|---|---|---|---|---|---|
| Calculated | 48.01 | 2.37 | 3.29 | 31.27 | 15.05 |
| Found | 48.05 | 2.39 | 3.29 | | |

SYNTHESIS EXAMPLE 15

Preparation of 2-propanoyloxy-5-(2,3,5,6-tetrafluoro-4-trifluoromethylbenzylamino)benzoic acid (15-1) Preparation of 5-tert-butoxycarbonylamino-2-propanoyloxybenzoic acid According to the similar procedure in Synthesis Example (14-2), by using propanoyl chloride (446 mg, 4.82 mmole), 0.71 g (57.0% yield) of was obtained 5-tert-butoxycarbonylamino-2-propanoyloxybenzoic acid as a white solid.

mp: 137-142° C., $^1$H-NMR(DMSO-d$_6$) δ 7.9~8.0 (s, 1H), 7.4~7.5 (d, 1H), 6.8~6.9 (d, 1H), 2.5~2.6 (t, 2H) 1.4~1.6 (s, 9H), 1.0~1.2(q, 3H), $^{13}$C NMR(DMSO-d$_6$) δ 172.689, 165.598, 152.804, 144.674, 137.287, 124.045, 79.618, 28.358, 27.259, 9.080

(15-2) Preparation of 5-amino-2-propanoyloxybenzoic acid

According to the similar procedure in Synthesis Example (14-3), by using 5-tert-butoxycarbonylamino-2-propanoyloxybenzoic acid (1.01 mg, 3.26 mmole), 0.67 g (97.0% yield) of was obtained 5-amino-2-propanoyloxybenzoic acid as a white solid.

mp: 213-220° C.,

1H-NMR(DMSO-d$_6$) δ 7.5~7.6 (s, 1H), 7.2~7.3 (d, 1H), 7.0~7.1 (d, 1H), 2.4~2.6 (t, 2H), 1.0~1.2 (q, 3H), $^{13}$C NMR(DMSO-d$_6$) δ 172.78, 165.35, 145.54, 137.100, 124.90, 124.76, 124.23, 121.72, 27.32, 9.10.

(15-3) Preparation of 2-propanoyloxy-5-(2,3,5,6-tetrafluoro-4-trifluoromethylbenzylamino) benzoic acid According to the similar procedure in Synthesis Example 14-4, by using 5-amino-2-propanoyloxybenzoic acid (0.32 g, 1.53 mmole) which was prepared from Synthesis Example (15-2), DMF (10 ml), TEA (0.05 ml), tetrabutyl ammonium iodide (3 mg), and 2,3,5,6-tetrafluoro-4-trifluoromethylbenzyl bromide (0.38 ml, 2.30 mmole), 0.34 g (51.0% yield) of was obtained 2-propanoyloxy-5-(2,3,5,6-tetrafluoro-4-trifluoromethylbenzylamino)benzoic acid as a white solid.

mp 188-191° C., $^1$H-NMR(acetone-d$_6$) δ 1.17 (t, 3H), 2.06 (q, 2H), 4.67(s, 2H), 6.94 (m, 2H), 7.37 (s, 1H), $^{13}$C NMR(acetone-d$_6$) δ 8.65, 27.41, 36.34, 114.76, 117.27, 123.57, 124.16, 124.59, 141.56, 142.44, 145.29, 145.31, 165.29, 172.77, IR(KBr pellet) 3414, 1745, 1702, 1491 cm$^{-1}$ Elemental analysis for C$_{18}$H$_{18}$F$_7$NO$_4$

| | % C | % H | % N | % F | % O |
|---|---|---|---|---|---|
| Calculated | 49.22 | 2.75 | 3.19 | 30.27 | 14.57 |
| Found | 49.20 | 2.76 | 3.20 | | |

SYNTHESIS EXAMPLE 16

Preparation of 2-cyclohexanecarbonyloxy-5-(2,3,5,6-tetrafluoro-4-trifluoromethylbenzylamino) benzoic acid (16-1) Preparation of 5-tert-butoxycarbonylamino-2-cyclohexanecarbonyloxybenzoic acid According to the similar procedure in Synthesis Example (14-2), by using cyclohexylcarbonyl chloride (707 mg, 4.82 mmole), 0.72 g (49.0% yield) of was obtained 5-tert-butoxycarbonylamino-2-cyclohexanecarbonyloxybenzoic acid as a white solid.

mp: 68-74° C.,

1H-NMR(DMSO-d$_6$) δ 7.9~8.0 (s, 1H), 7.4~7.5 (d, 1H), 6.8~6.9 (d, 1H), 2.4~2.6 (t, 1H), 1.0~2.0 (m, 19H)

(16-2) Preparation of 5-amino-2-cyclohexanecarbonyloxybenzoic acid

According to the similar procedure in Synthesis Example 14-3, by using 5-tert-butoxycarbonylamino-2-cyclohexanecarbonyloxybenzoic acid (1.01 mg, 2.78 mmole), 0.70 g (96.0% yield) of was obtained 5-amino-2-cyclohexanecarbonyloxybenzoic acid as a white solid.

mp: 116-121° C., $^1$H-NMR(DMSO-d$_6$) δ 7.5~7.6 (s, 1H), 7.4~7.5 (d, 1H), 6.9~7.0 (d, 1H), 2.4~2.6 (t, 1H), 1.0~2.0 (m, 10H), $^{13}$C NMR(DMSO-d$_6$) 173.87, 170.74, 165.60, 160.09, 158.61, 158.27, 143.14, 140.71, 130.03, 124.66, 123.44, 121.70, 119.12, 118.61, 113.81, 42.42, 31.25, 28.94, 25.65, 22.38, 14.29.

(16-3) Preparation of 2-cyclohexanecarbonyloxy-5-(2,3,5,6-tetrafluoro-4-trifluoromethylbenzylamino)benzoic acid According to the similar procedure in Synthesis Example (14-4), by using 5-amino-2-cyclohexanecarbonyloxybenzoic acid (1.03 g, 3.95 mmole) which was prepared from Synthesis Example (16-2), DMF (15 ml), TEA (0.10 ml), tetrabutyl ammonium iodide (10 mg), and 2,3,5,6-tetrafluoro-4-trifluoromethylbenzyl bromide (1.01 ml, 5.92 mmole), 0.95 g (49.0% yield) of was obtained 2-cyclohexanecarbonyloxy-5-(2,3,5,6-tetrafluoro-4-trifluoromethylbenzylamino)benzoic acid as a white solid.

mp 190-193° C., $^1$H-NMR(acetone-d$_6$) δ 1.20~1.57 (m, 6H), 1.64~1.81 (m, 4H) 2.53 (m, 1H), 4.67 (s, 2H), 6.90 (d, 1H), 6.96 (d, 1H), 7.36(S, 1H), $^{13}$C NMR(acetone-d$_6$) δ 25.57, 26.07, 36.23, 43.13, 114.67, 117.21, 122.21, 122.36, 124.45, 124.56, 142.32, 142.74, 144.21, 145.24, 146.82, 165.29, 173.96, IR(KBr pellet) 3402, 1724, 1707, 1491 cm$^{-1}$

| Elemental analysis for $C_{22}H_{18}F_7NO_4$ | | | | | |
|---|---|---|---|---|---|
| | % C | % H | % N | % F | % O |
| Calculated | 53.56 | 3.68 | 2.84 | 26.96 | 12.97 |
| Found | 53.58 | 3.65 | 2.85 | | |

BRIEF DESCRIPTION OF THE DRAWINGS

The above and other objects, features and other advantages of the present invention will be more clearly understood from the following detailed description taken in conjunction with the accompanying drawings, in which.

Mouse cortical cell cultures (DIV 12-14) were exposed to 300 μM NMDA for 10 min, alone or with inclusion of 3-300 μM 2-Hydroxy-TTBA. Neuronal death was analyzed 24 hr later by measuring levels of LDH released into the bathing medium, mean±SEM (n=9-12 culture wells per condition), scaled to mean LDH efflux value 24 hr after sham wash (=0) and continuous exposure to 500 μM NMDA (=100) that causes near complete neuronal death. *, Significant difference from the vehicle control, $p<0.05$ using ANOVA and Student-Neuman-Keuls' test.

Figure 1A:
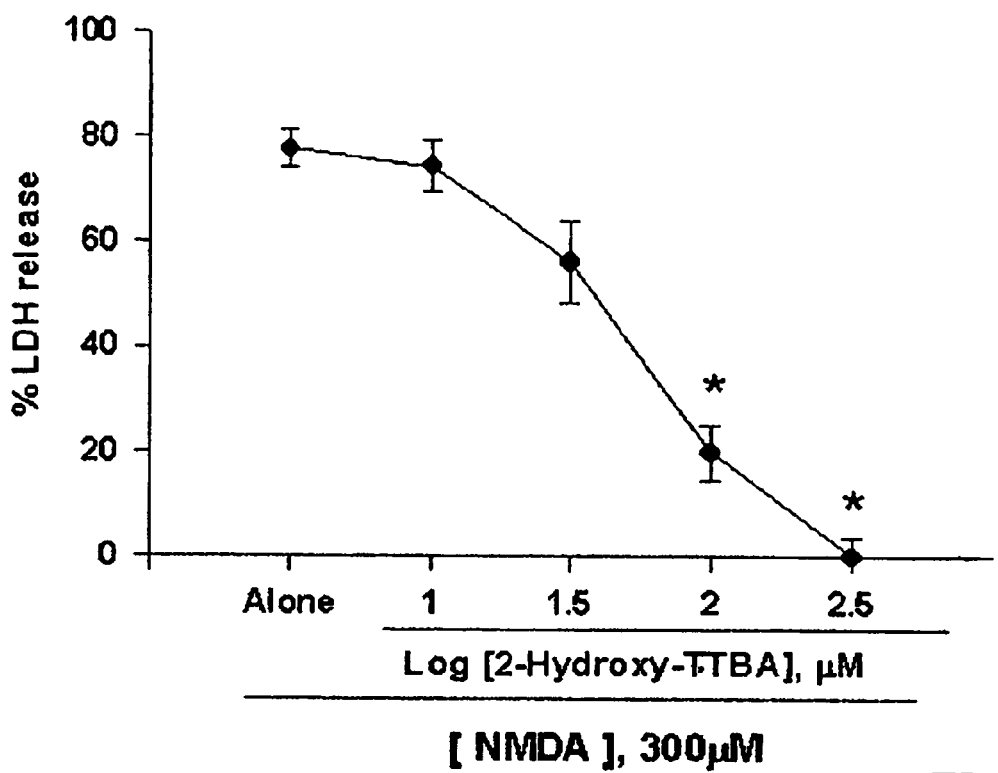
FIG. 1a. The effect of 2-Hydroxy-TTBA on NMDA-induced excitotoxicity.
Figure 1B:
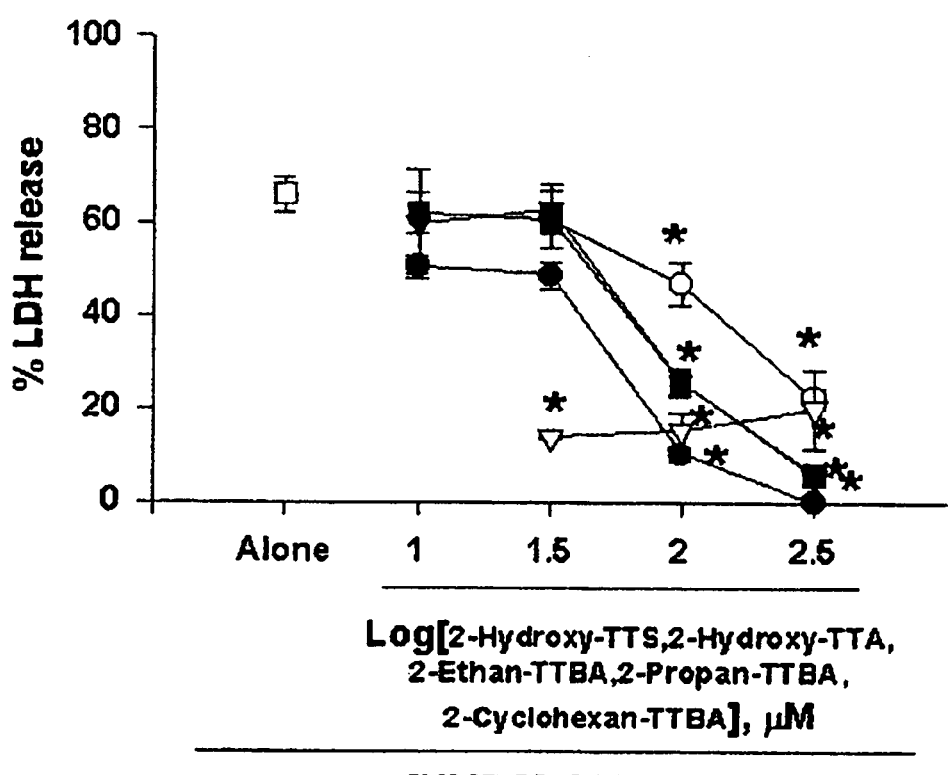

FIG. 1b. The effect of 2-Hydroxy-TTS, 2-Hydroxy-TTA, 2-Ethan-TTBA, 2-Propan-TTBA, or 2-Cyclohexan-TTBA on NMDA-induced excitotoxicity.

Mouse cortical cell cultures (DIV 12-14) were exposed to 300 μM NMDA for 10 min, alone (□) or with inclusion of 3-300 μM 2-Hydroxy-TTS (●), 2-Hydroxy-TTA (○), 2-Ethan-TTBA (▼), 2-Propan-TTBA (▽), or 2-Cyclohexan-TTBA (■). Neuronal death was analyzed 24 hr later by measuring levels of LDH released into the bathing medium, mean±SEM (n=9-12 culture wells per condition), scaled to mean LDH efflux value 24 hr after sham wash (=0) and continuous exposure to 500 μM NMDA (=100). *, Significant difference from the vehicle control, $p<0.05$ using ANOVA and Student-Neuman-Keuls' test.

FIG. 2a. Blockade of NMDA currents by 2-Hydroxy-TTBA.

Typical NMDA-induced inward currents (NMDA currents) were evoked by applying 300 μM NMDA to cortical neurons which were held at −60 mV. Successive application of various concentrations of 2-Hydroxy-TTBA reduced the response elicited by 300 μM NMDA in a concentration-dependent manner (n=8). The graph shows a dose response relation of 2-Hydroxy-TTBA to NMDA currents; its $IC_{50}$ value was close to 35 μM and Hill coefficient 0.91.

FIG. 2b. Pretreatment with 2-Hydroxy-TTBA did not influence NMDA currents.

Cortical neurons were treated with 100 μM 2-Hydroxy-TTBA, washed thoroughly, and then applied with 300 μM NMDA. The pretreatment with 2-Hydroxy-TTBA did not influence NMDA-induced inward currents, suggesting that 2-Hydroxy-TTBA exert its blocking action only when the receptor has been activated by agonist (n=6).

Figure 3A:
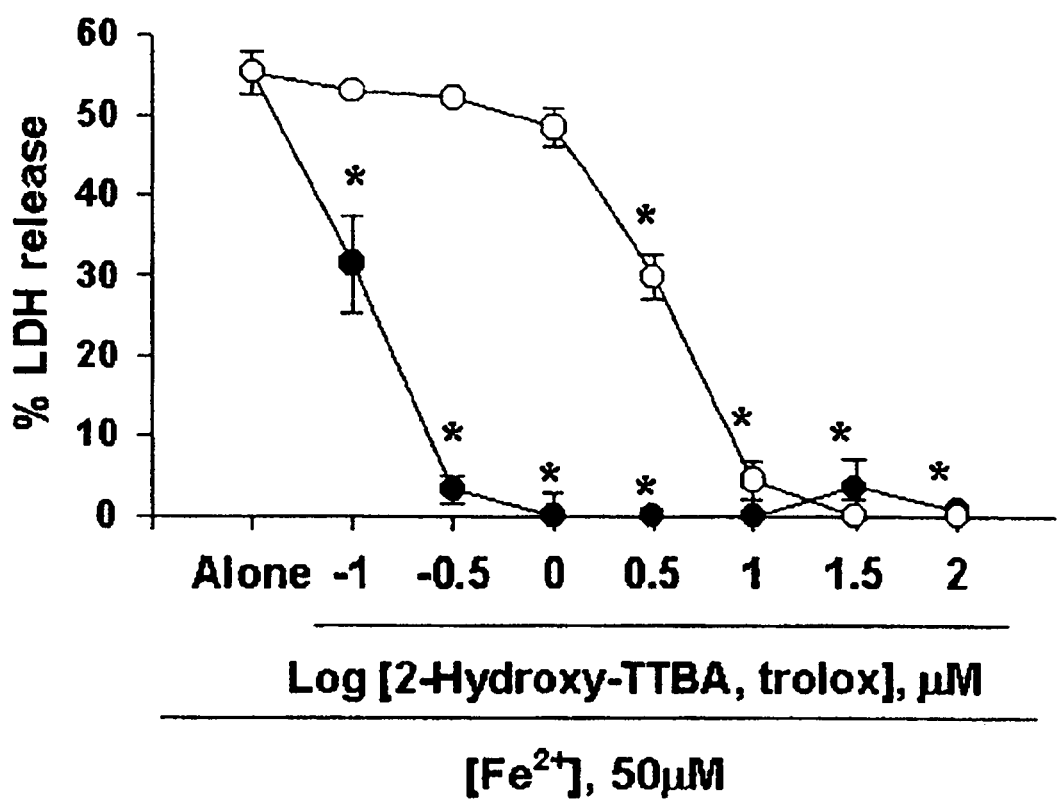

FIG. 3a. The effect of 2-Hydroxy-TTBA on $FeCl_2$-induced oxidative stress.

Mouse cortical cell cultures (DIV 12-14) were exposed to continuously to 50 μM $Fe^{2+}$, alone or with inclusion of 0.1-100 μM 2-Hydroxy-TTBA (●) or trolox (○), a membrane-permeable form of vitamin E). Neuronal death was analyzed 24 hr later by measuring levels of LDH released into the bathing medium, mean±SEM (n=9-12 culture wells per condition), scaled to mean LDH efflux value 24 hr after sham wash (=0) and continuous exposure to 500 μM NMDA (=100). *, Significant difference from the vehicle control, $p<0.05$ using ANOVA and Student-Neuman-Keuls' test.

Figure 3B:
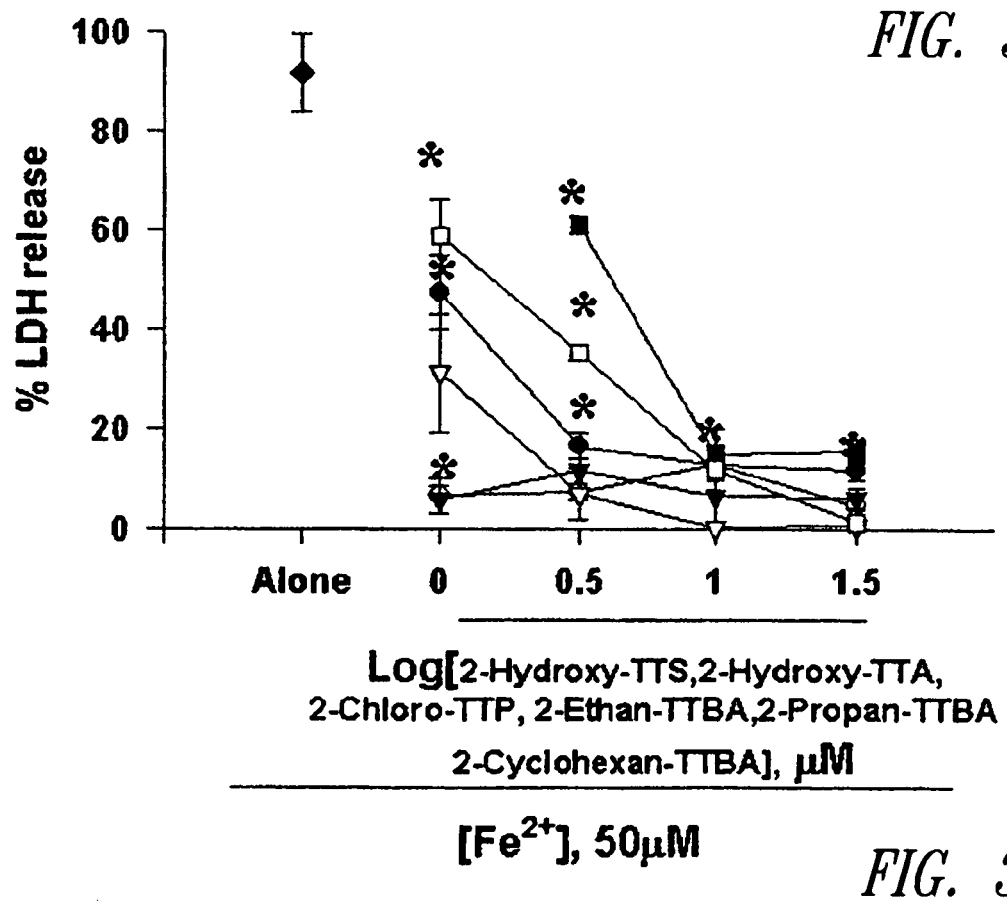

FIG. 3b. The effect of 2-Hydroxy-TTS, 2-Hydroxy-TTA, 2-Chloro-TTP, 2-Ethan-TTBA, 2-Propan-TTBA, or 2-Cyclohexan-TTBA on $FeCl_2$-induced oxidative stress.

Mouse cortical cell cultures (DIV 12-14) were exposed to continuously to 50 μM $Fe^{2+}$, alone (♦) or with inclusion of 1-30 μM 2-Hydroxy-TTS (●), 2-Hydroxy-TTA (○), 2-Chloro-TTP (▼), 2-Ethan-TTBA (▽), 2-Propan-TTBA (■), or 2-Cyclohexan-TTBA (□). Neuronal death was analyzed 24 hr later by measuring levels of LDH released into the bathing medium, mean±SEM (n=9-12 culture wells per condition), scaled to mean LDH efflux value 24 hr after sham wash (=0) and continuous exposure to 500 μM NMDA (=100). *, Significant difference from the vehicle control, $p<0.05$ using ANOVA and Student-Neuman-Keuls' test.

Figure 4:
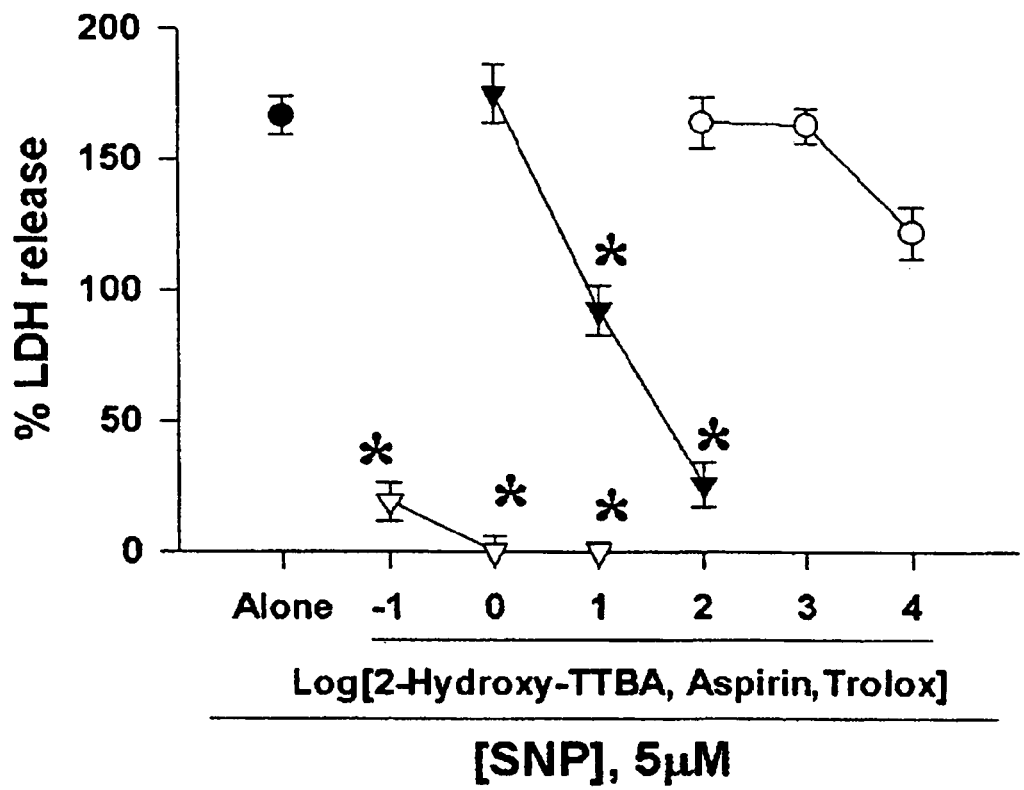

FIG. 4. The effect of 2-Hydroxy-TTBA on SNP-induced oxidative stress.

Mouse cortical cell cultures (DIV 12-14) were exposed to continuously 5 μM sodium nitroprusside (SNP), alone (●) or with inclusion of 0.1-10 mM aspirin (○), 1-100 μM trolox (▼), or 0.1-10 M 2-Hydroxy-TTBA (▽). Neuronal death was analyzed 24 hr later by measuring levels of LDH released into the bathing medium, mean±SEM (n=9-12 culture wells per condition), scaled to mean LDH efflux value 24 hr after sham wash (=0) and continuous exposure to 500 μM NMDA (=100). *, Significant difference from the vehicle control, $p<0.05$ using ANOVA and Student-Neuman-Keuls' test.

Figure 5:
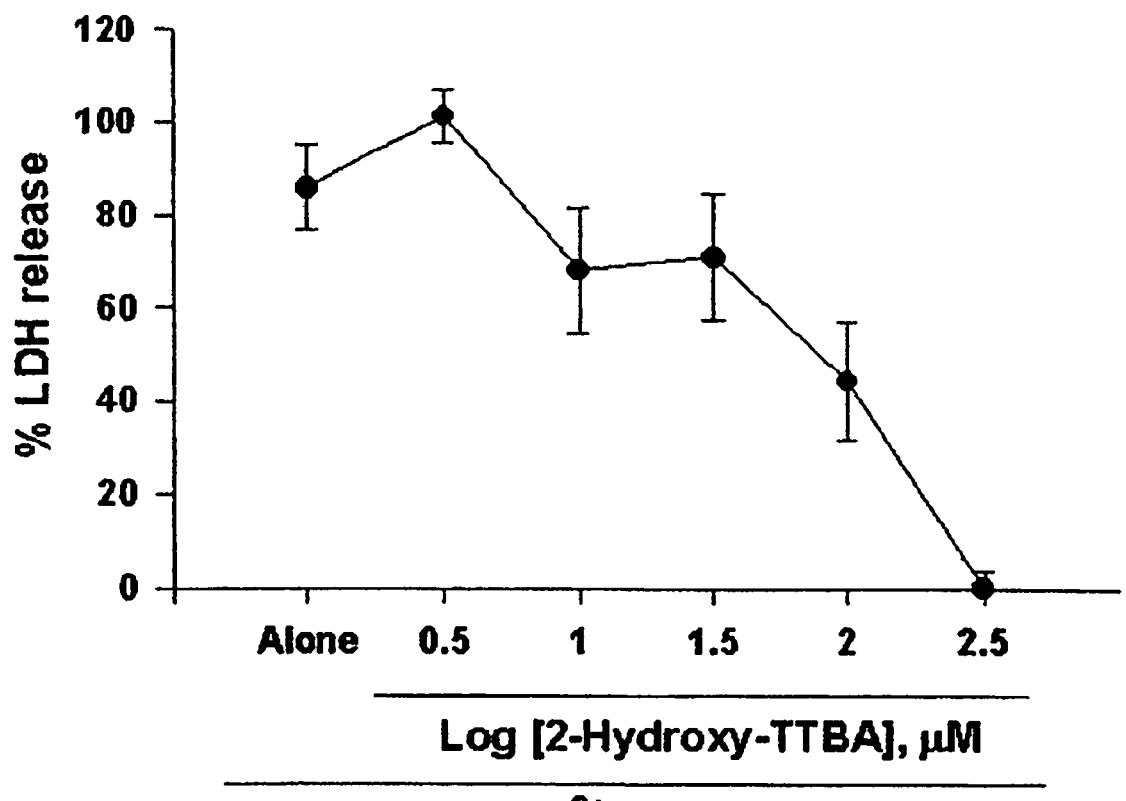

FIG. 5. The effect of 2-Hydroxy-TTBA on zinc toxicity.

Mouse cortical cell cultures (DIV 12-14) were exposed to 300 μM $Zn^{2+}$ for 30 min, alone or with inclusion of 3-300 μM 2-Hydroxy-TTBA. Neuronal death was analyzed 24 hr later by measuring levels of LDH released into the bathing medium, mean±SEM (n=9-12 culture wells per condition), scaled to mean LDH efflux value 24 hr after sham wash (=0) and continuous exposure to 500 μM NMDA (=100).

Figure 6A:
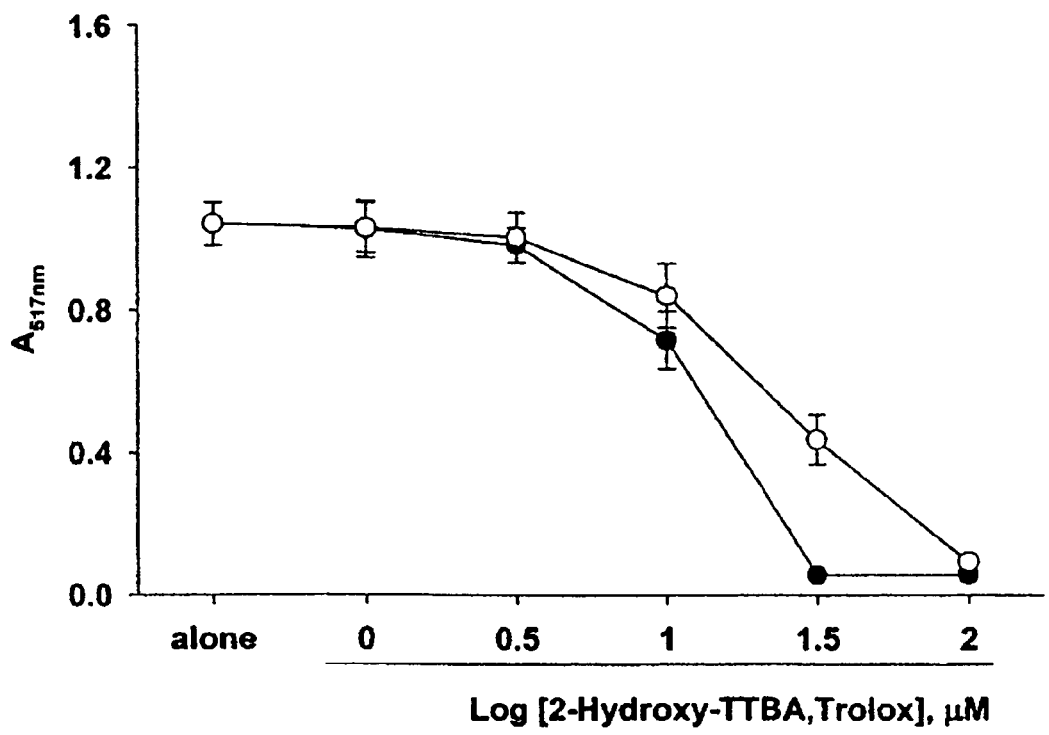

FIG. 6a. Free radical scavenging activity of 2-Hydroxy-TTBA.

2-Hydroxy-TTBA (●) or trolox (○) was reacted with 100 uM 1,1-diphenyl-2-picrylhydrazil (DPPH, a stable free radical) dissolved in ethanol for 10 min. The radical scavenging activity was determined by measuring the decrease in DPPH levels at 517 nm. *, Significant difference from the vehicle control, $p<0.05$ using ANOVA and Student-Neuman-Keuls' test.

Figure 6B:
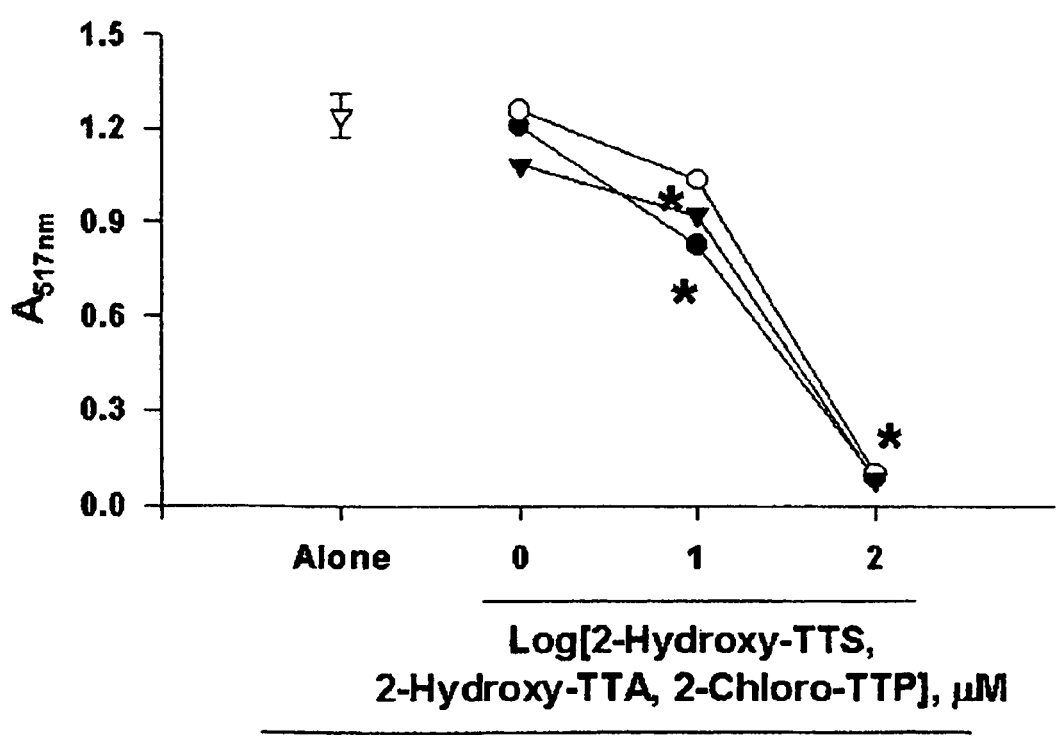

FIG. 6b. The DPPH assay of 2-Hydroxy-TTS, 2-Hydroxy-TTA, or 2-Chloro-TTP.

2-Hydroxy-TTS (●) 2-Hydroxy-TTA (○), 2-Chloro-TTP (▼) or control (▽) was reacted with 100 uM DPPH dissolved in ethanol. The radical scavenging activity was determined by measuring the decrease in DPPH levels at 517 nm. * Significant difference from the vehicle control, $p<0.05$ using ANOVA and Student-Neuman-Keuls' test.

Figure 7A:
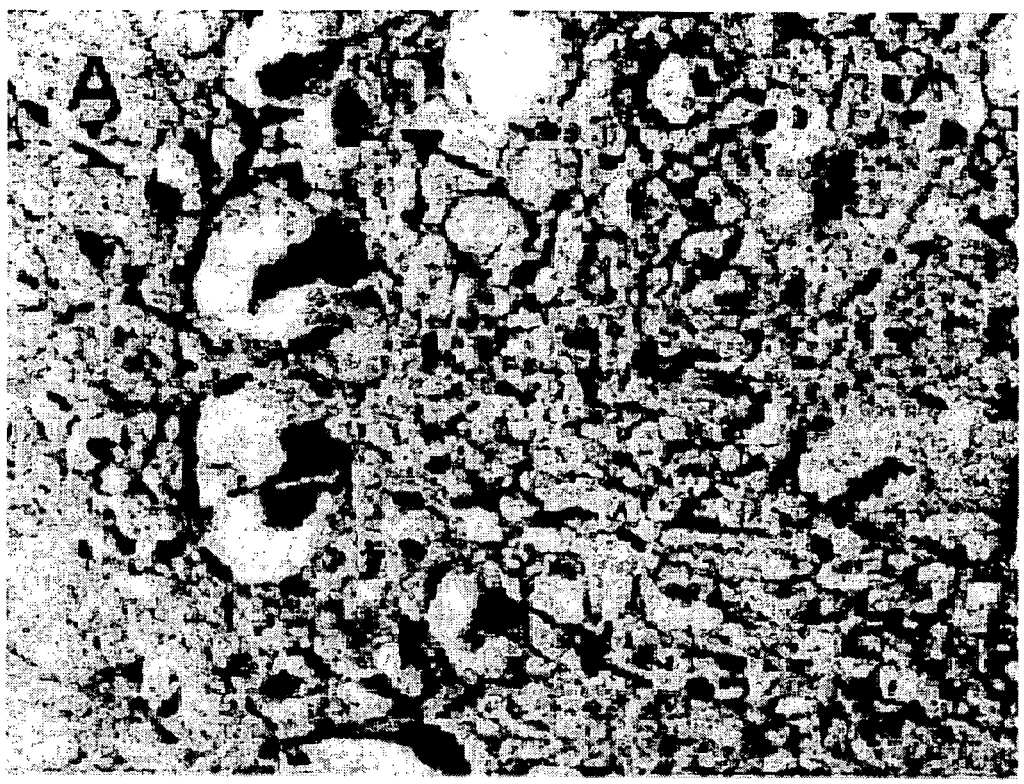
Figure 7A:
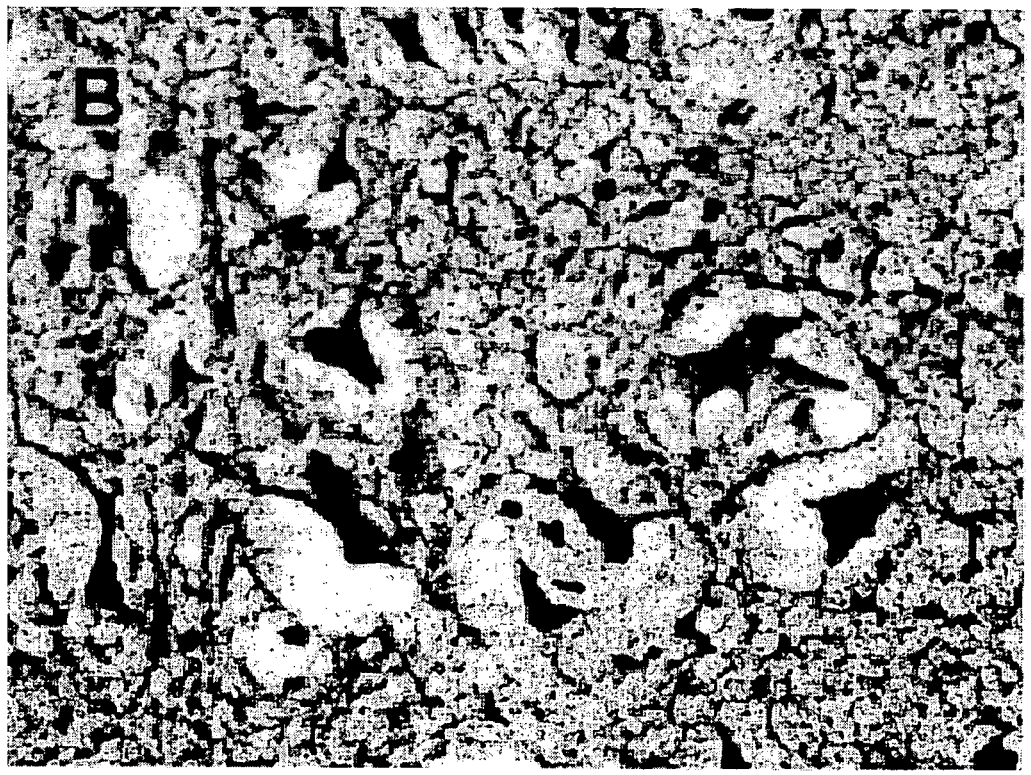

FIG. 7a. 2-Hydroxy-TTBA reduces neuronal death in the spinal cord in an animal model of ALS.

Bright field photomicrographs of spinal cord sections stained with eosin from amyotrophic lateral sclerosis (ALS) mice over expressing the mutant SOD1-G93A that received vehicle (A) or 2-Hydroxy-TTBA (B, 10 mg/kg/day through drinking water) for 8 weeks from the age of 2 months.

Figure 7B:
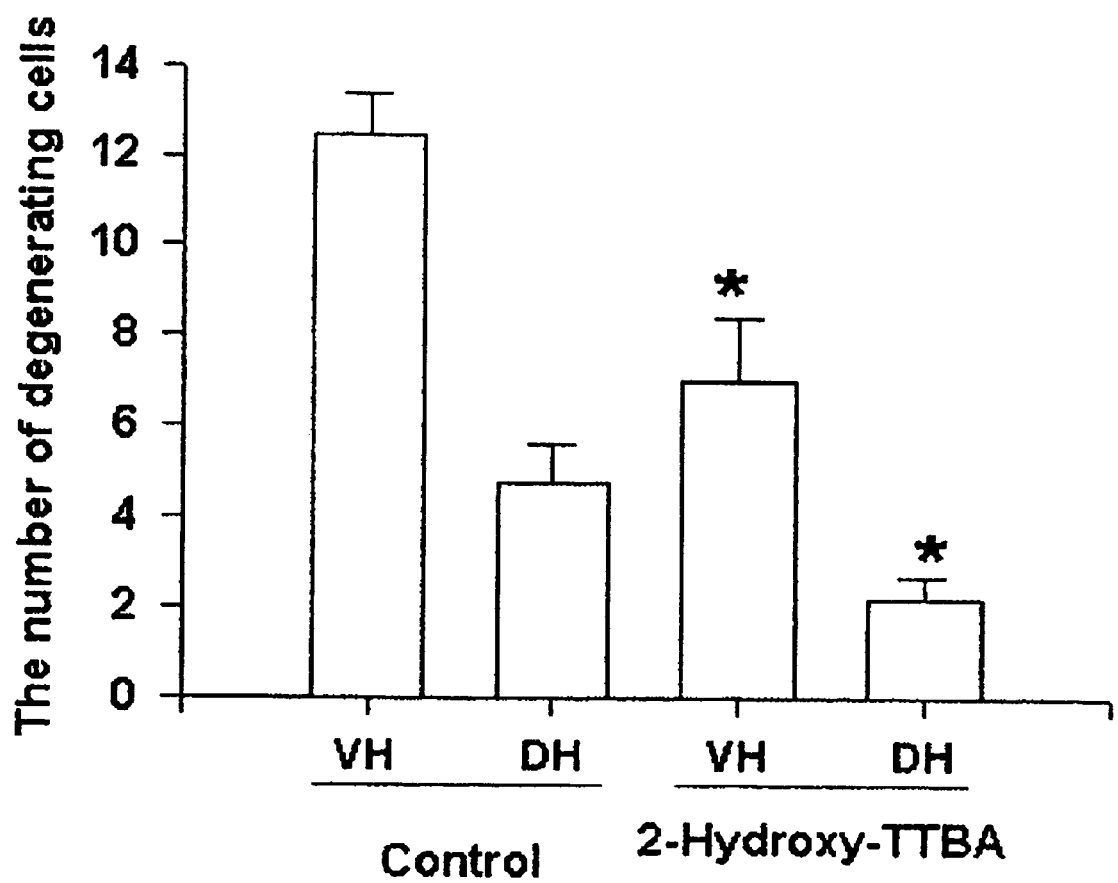

FIG. 7b. 2-Hydroxy-TTBA reduces neuronal death in the spinal cord in an animal model of ALS.

Degenerating neurons from FIG. 7a. were analyzed by counting viable neurons after staining with eosin in the dorsal and ventral horn of spinal cord from ALS mice treated with a vehicle (Control) or 2-Hydroxy-TTBA, mean±S.E.M (n=5 animals for each condition). *, Significant difference from the vehicle control, p<0.05 using the independent t-test.

Figure 8A:
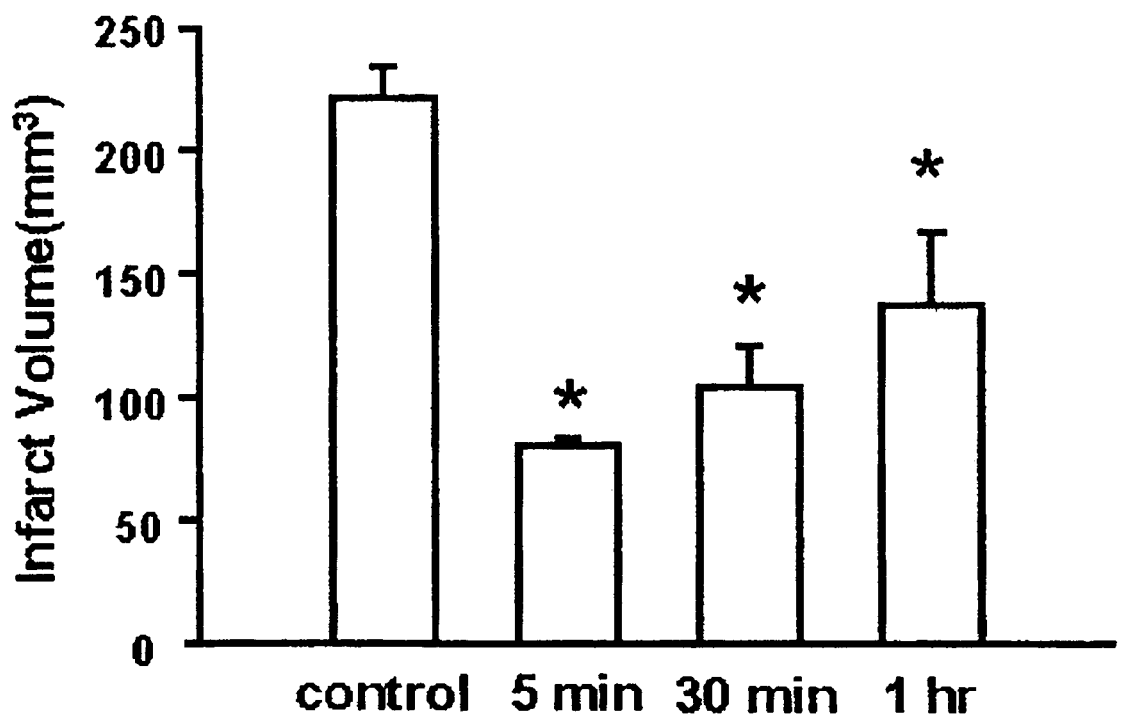

FIG. 8a. Intraperitoneal administration of 2-Hydroxy-TTBA reduces ischemic injury in brain.

Adult rats received transient cerebral ischemia by occluding right middle cerebral artery and both common carotid arteries for 60 min with intraperitoneal injections of vehicle or 50 mg/kg 2-Hydroxy-TTBA at 5 min, 30 min, or 1 hr after reperfusion. Infarct volume was analyzed 24 hr later after staining brain slices with 2% 2,3,5-triphenyltetrazolium chloride (TTC), mean ±SEM (n=8-11 rats per each condition). *, Significant difference from the vehicle control, p<0.05 using ANOVA and Student-Neuman-Keuls' test.

Figure 8B:
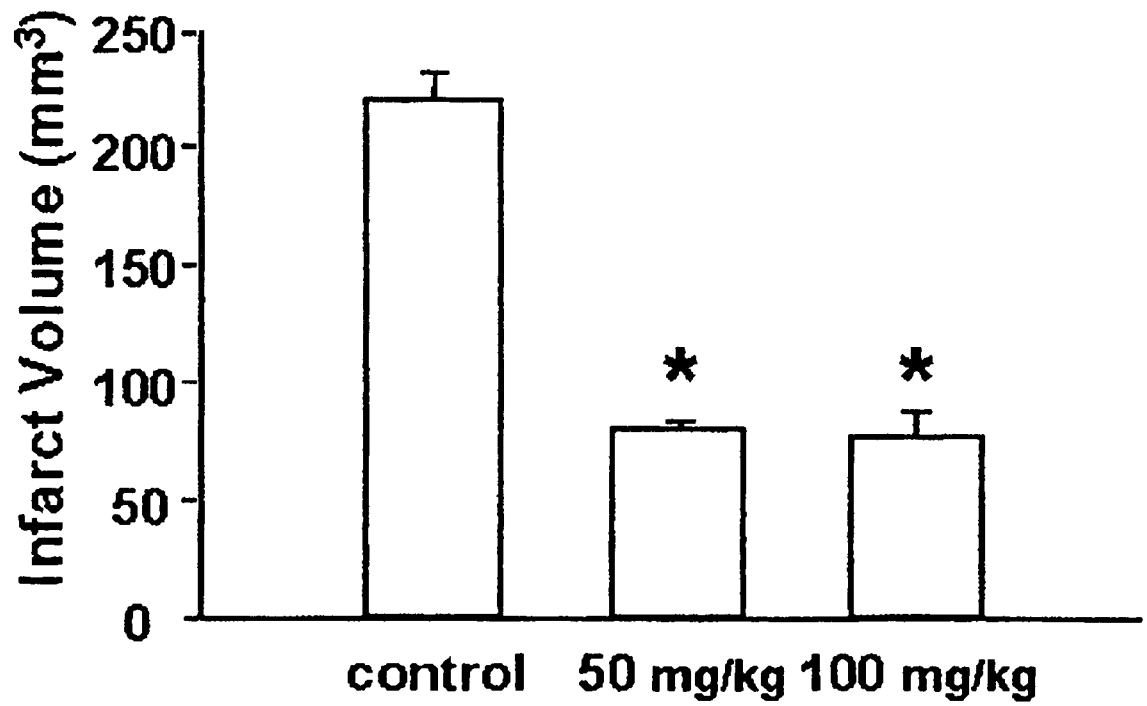

FIG. 8b. Intraperitoneal administration of 2-Hydroxy-TTBA reduces ischemic injury in brain.

Adult rats received transient cerebral ischemia by occluding right middle cerebral artery and both common carotid arteries for 60 min with intraperitoneal injections of vehicle (control) or 50 or 100 mg/kg 2-Hydroxy-TTBA at 5 min after reperfusion. Infarct volume was analyzed 24 hr later after staining brain slices with 2% 2,3,5-triphenyltetrazolium chloride (TTC), mean±SEM (n=7-8 rats per each condition). *, Significant difference from the vehicle control, p<0.05 using ANOVA and Student-Neuman-Keuls' test.

Figure 8C:
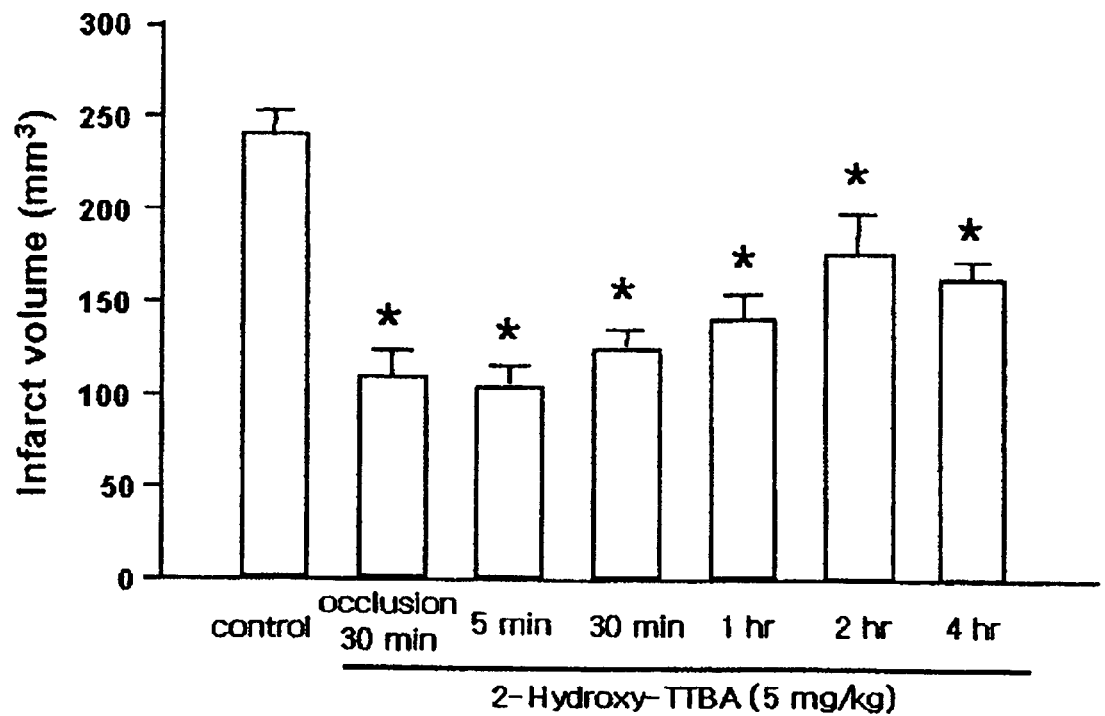

FIG. 8c. Intravenous injections of 2-Hydroxy-TTBA reduces ischemic injury in brain.

Adult rats received transient cerebral ischemia by occluding right middle cerebral artery and both common carotid arteries for 60 min, with intravenous injections of vehicle (control) or 5 mg/kg 2-Hydroxy-TTBA at 30 min after occlusion or 5 min, 3.0 min, 1 hr, 2 hr, or 4 hr after reperfusion. Infarct volume was analyzed 24 hr later, mean±SEM (n=8-11 rats per each condition). *, Significant difference from the vehicle control, p<0.05 using ANOVA and Student-Neuman-Keuls' test.

Figure 8D:
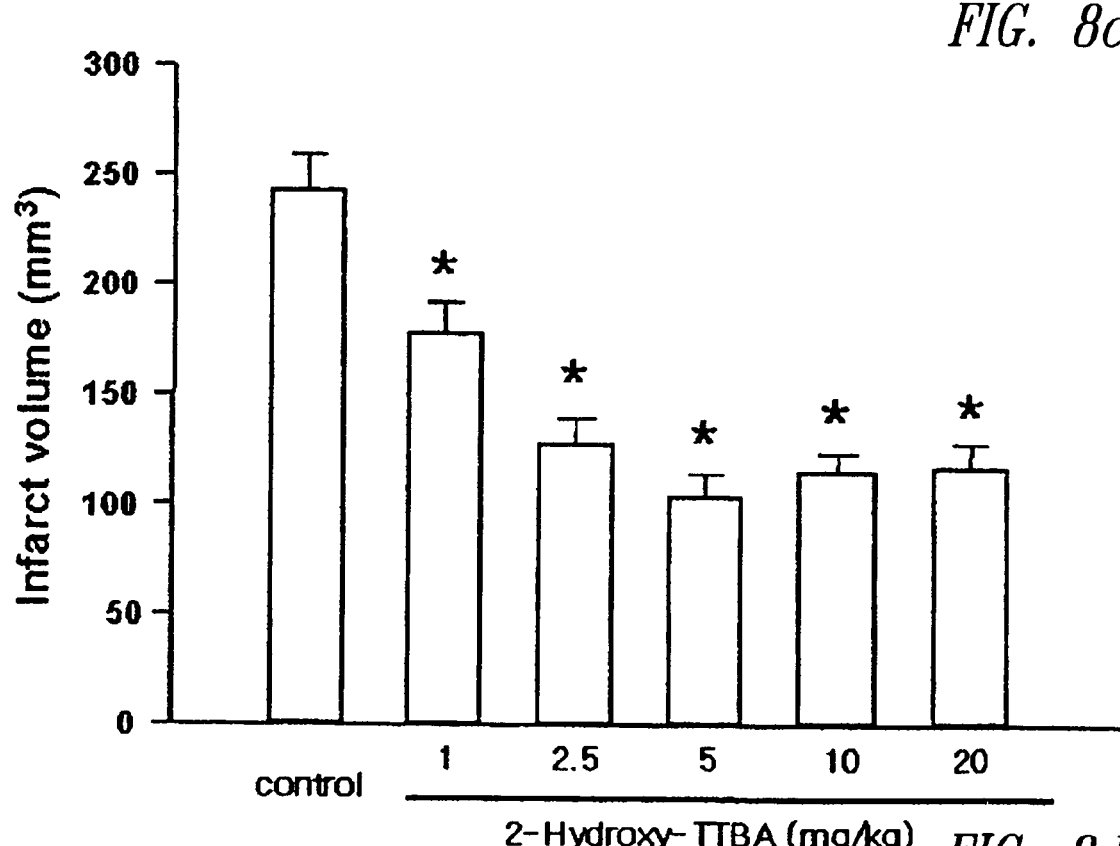

FIG. 8d. Intravenous injections of 2-Hydroxy-TTBA reduces ischemic injury in brain.

Adult rats received transient cerebral ischemia by occluding right middle cerebral artery and both common carotid arteries for 60 min, with intravenous injections of vehicle (control) or 1, 2.5, 5, 10 or 20 mg/kg 2-Hydroxy-TTBA at 5 min after reperfusion. Infarct volume was analyzed 24 hr later, mean±SEM (n=8-10 rats per each condition). *, Significant difference from the vehicle control, p<0.05 using ANOVA and Student-Neuman-Keuls' test.

Figure 8E:
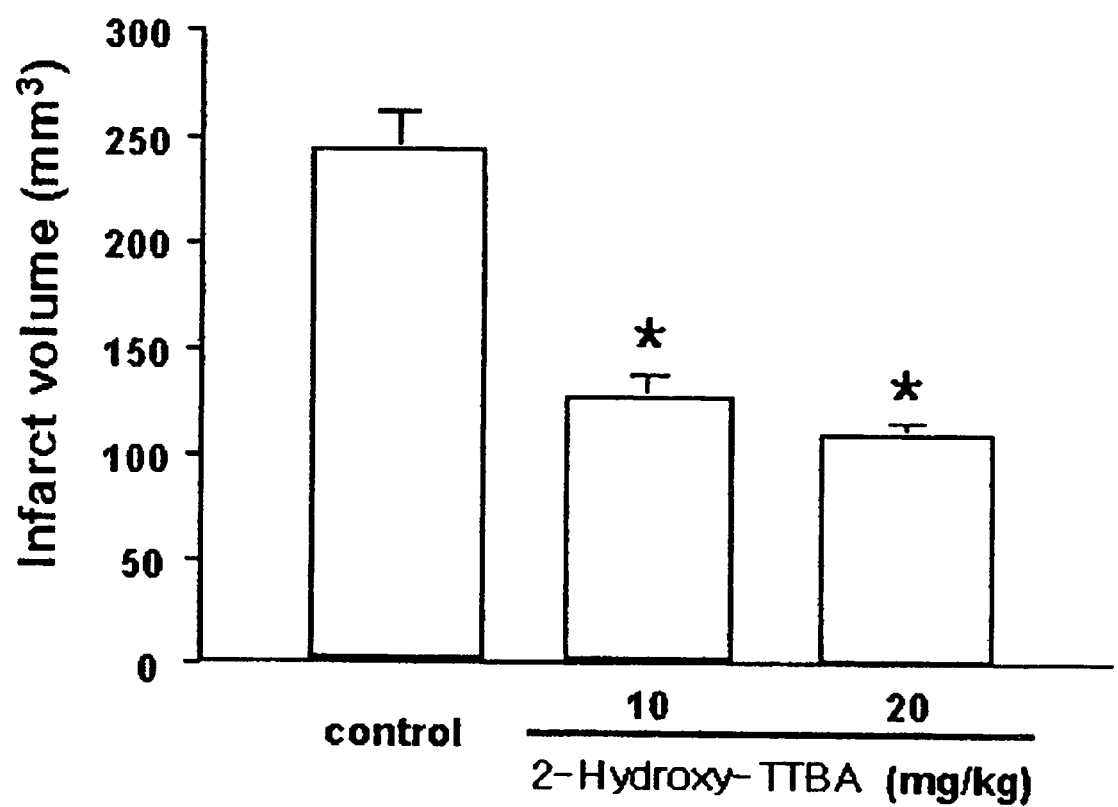

FIG. 8e. Oral administration of 2-Hydroxy-TTBA reduces ischemic injury in brain.

Adult rats received transient cerebral ischemia by occluding right middle cerebral artery and both common carotid arteries for 60 min, with oral administrations of vehicle (control) or 10 or 20 mg/kg 2-Hydroxy-TTBA at 5 min after reperfusion. Infarct volume was analyzed 24 hr later, mean±SEM (n=8-10 rats per each condition). *, Significant difference from the vehicle control, p<0.05 using ANOVA and Student-Neuman-Keuls' test.

Figure 9A:
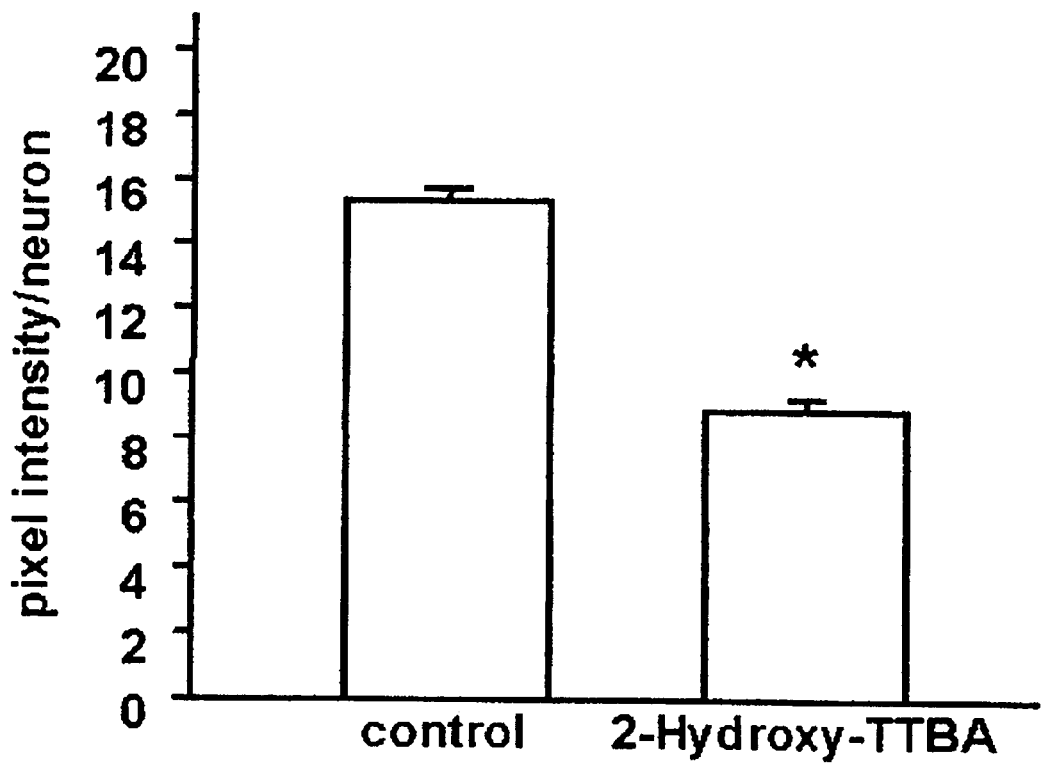

FIG. 9a. Effects of 2-Hydroxy-TTBA on mitochondrial ROS generation at 72 hr of recirculation after global ischemia.

Mitotracker CM-$H_2X$ ROS was injected into the lateral ventricle of rat brain at 24 hr before ischemic surgery, and then animals received transient forebrain ischemia for 10 min, with intraperitoneal injections of vehicle (control) or 2-Hydroxy-TTBA (50 mg/kg) at 5 min after reperfusion. The levels of mitochondrial ROS were analyzed 2 hr later, mean±S.E.M. (n=50-70 neurons randomly chosen from the CA1 sector of the hippocampal formation per each condition). Significant difference from the vehicle control, p<0.05 using the independent t-test.

Figure 9B:
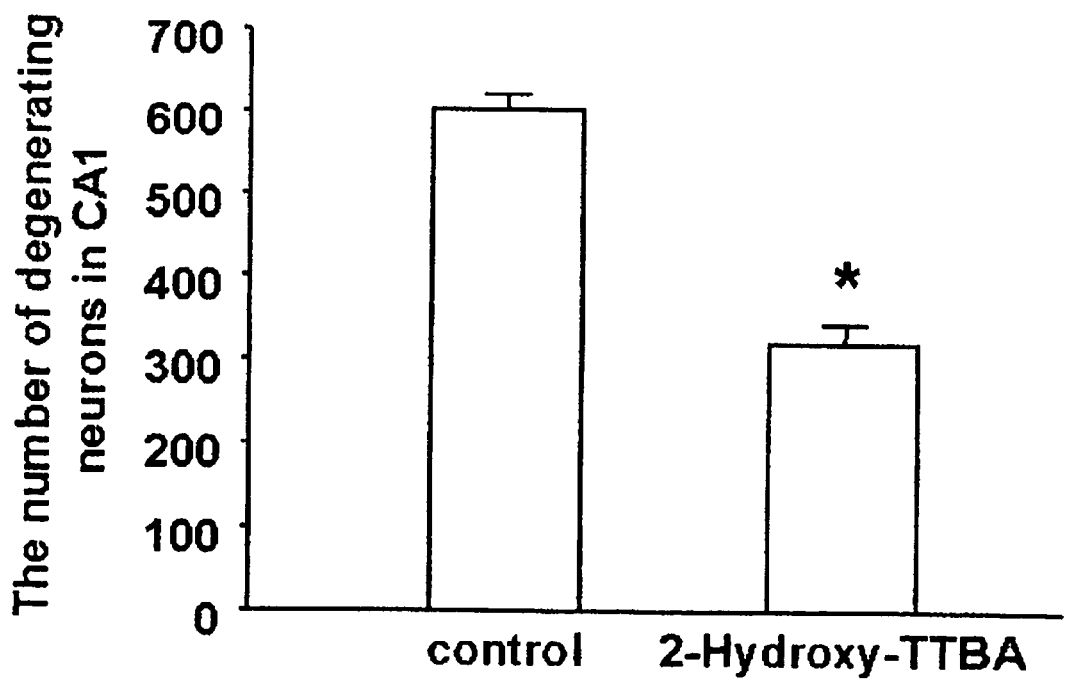

FIG. 9b. 2-Hydroxy-TTBA prevents neuronal death in the CA1 sector at 72 hr of recirculation after global ischemia.

Adult rats received transient global ischemia for 10 min, with intraperitoneal injections of vehicle (control) or 2-Hydroxy-TTBA (50 mg/kg) at 5 min. after reperfusion. The number of degenerating neurons in the CA1 was analyzed 3 d later by counting viable neurons after staining with cresyl violet, mean±S.E.M. *, Significant difference from the vehicle control, p<0.05 using the independent t-test.

Figure 10A:
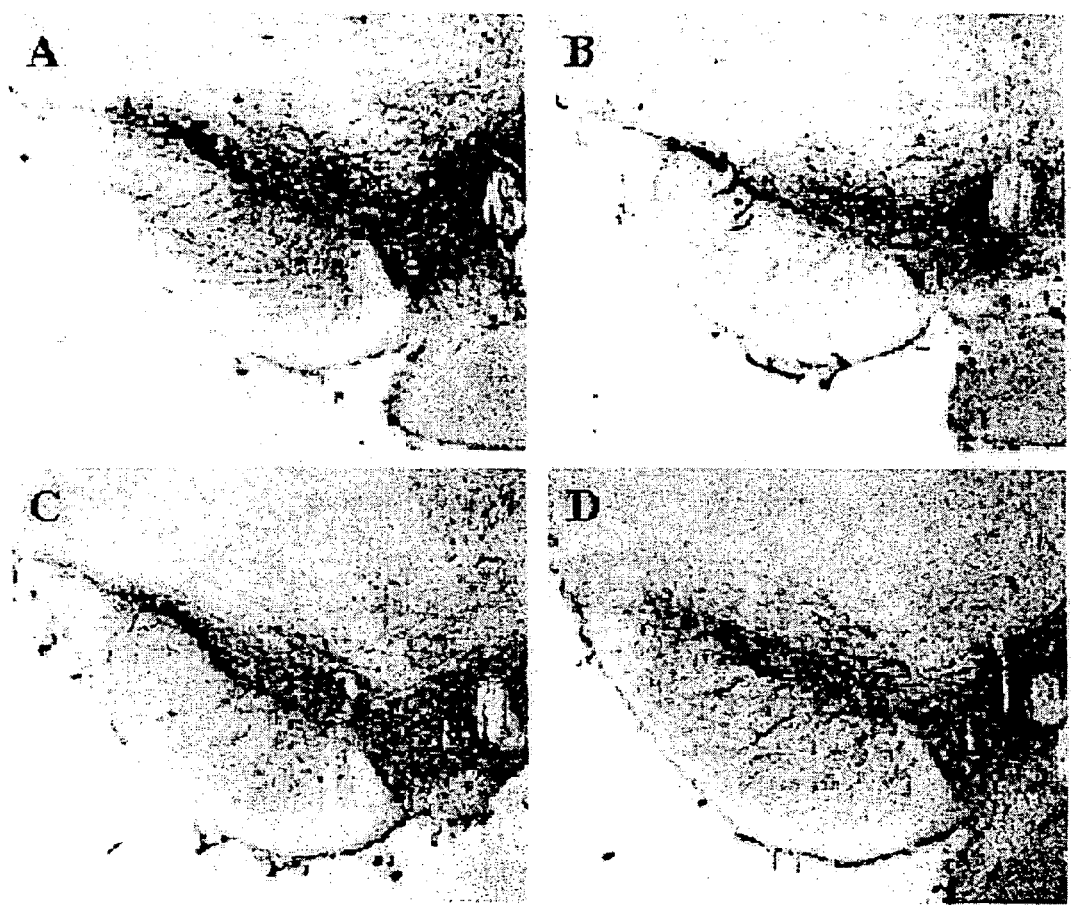

FIG. 10a. 2-Hydroxy-TTBA reduces death of dopaminergic neurons in the substantia nigra 3 d following MPTP injection.

Bright field photomicrographs showing dopaminergic neurons in the substantia nigra immunostained with anti-tyrosine hydroxylase (TH) antibody 3 d following sham control (A) or the single daily injection of 1-methyl-4-phenyl-1,2,3,6-tetra-hydropyridine (MPTP, 40 mg/kg, SC) in C57/BL6 mice, alone (B) or with intraperitoneal injections (2 times per day) of 2-Hydroxy-TTBA (C, 25 mg/kg; D, 50 mg/kg) prior to MPTP administration.

Figure 10B:
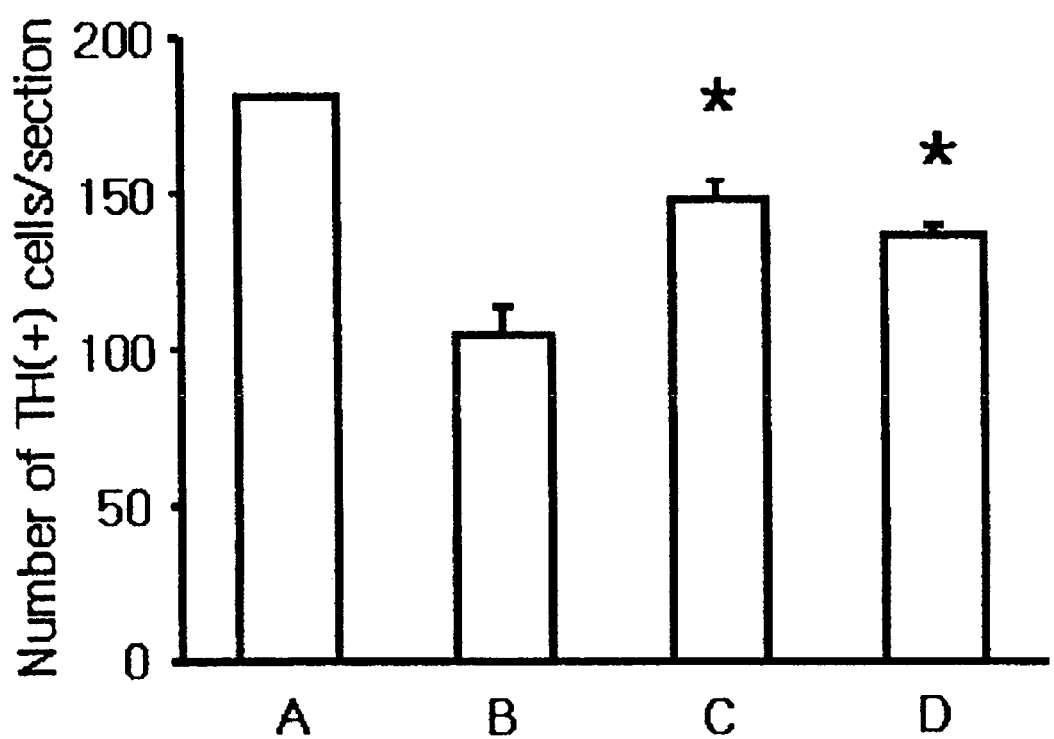

FIG. 10b. 2-Hydroxy-TTBA reduces death of dopaminergic neurons in the substantia nigra 3 d following MPTP injection.

Quantification of TH-positive dopaminergic neurons in the substantia nigral sections 3 d following the single daily injection of (MPTP, 40 mg/kg, SC), alone or with pretreatment with 2-Hydroxy-TTBA as described above. *, Significant difference from the control, p<0.05 using ANOVA and Student-Neuman-Keuls' test.

Figure 10C:
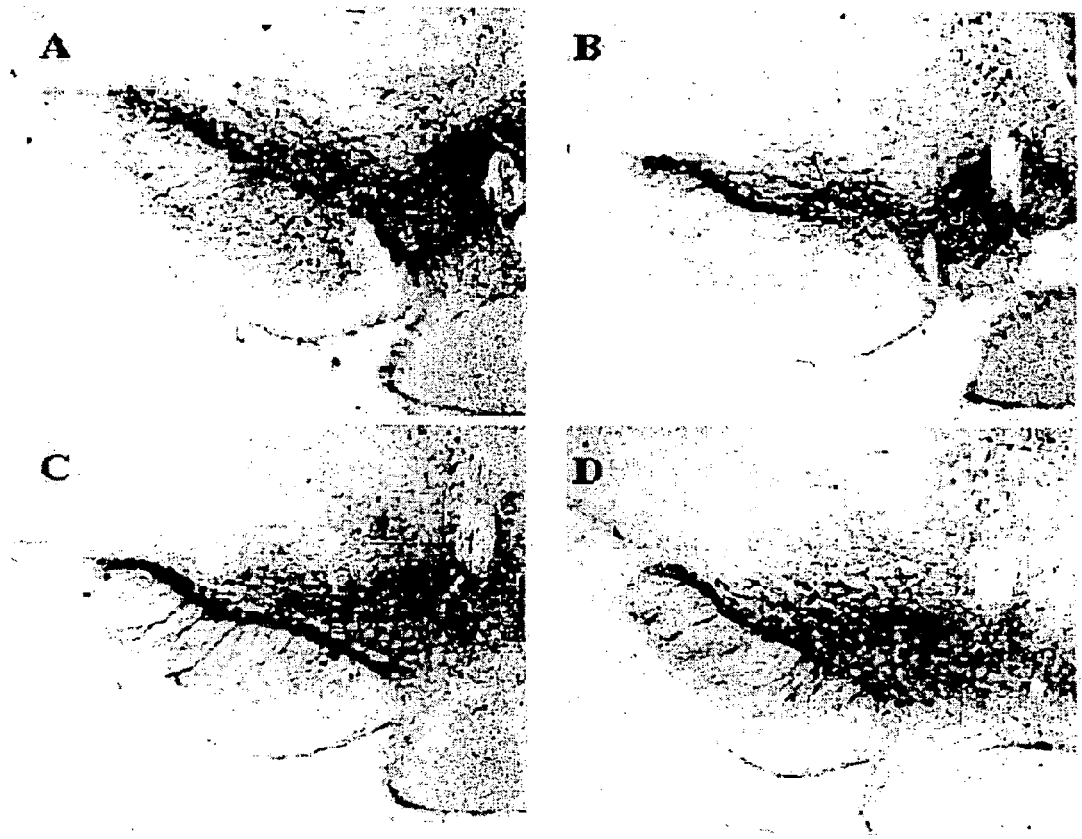

FIG. 10c. 2-Hydroxy-TTBA reduces death of dopaminergic neurons in the substantia nigra 7 d following MPTP injection.

Bright field photomicrographs showing dopaminergic neurons in the substantia nigra immunostained with anti-tyrosine hydroxylase (TH) antibody 7 d following sham control (A) or the single daily injection of 1-methyl-4-phenyl-1,2,3,6-tetra-hydropyridine (MPTP, 40 mg/kg, SC) in C57/BL6 mice, alone (B) or with intraperitoneal injections (2 times per day) of 2-Hydroxy-TTBA, (C, 25 mg/kg; D, 50 mg/kg) prior to MPTP administration.

Figure 11:
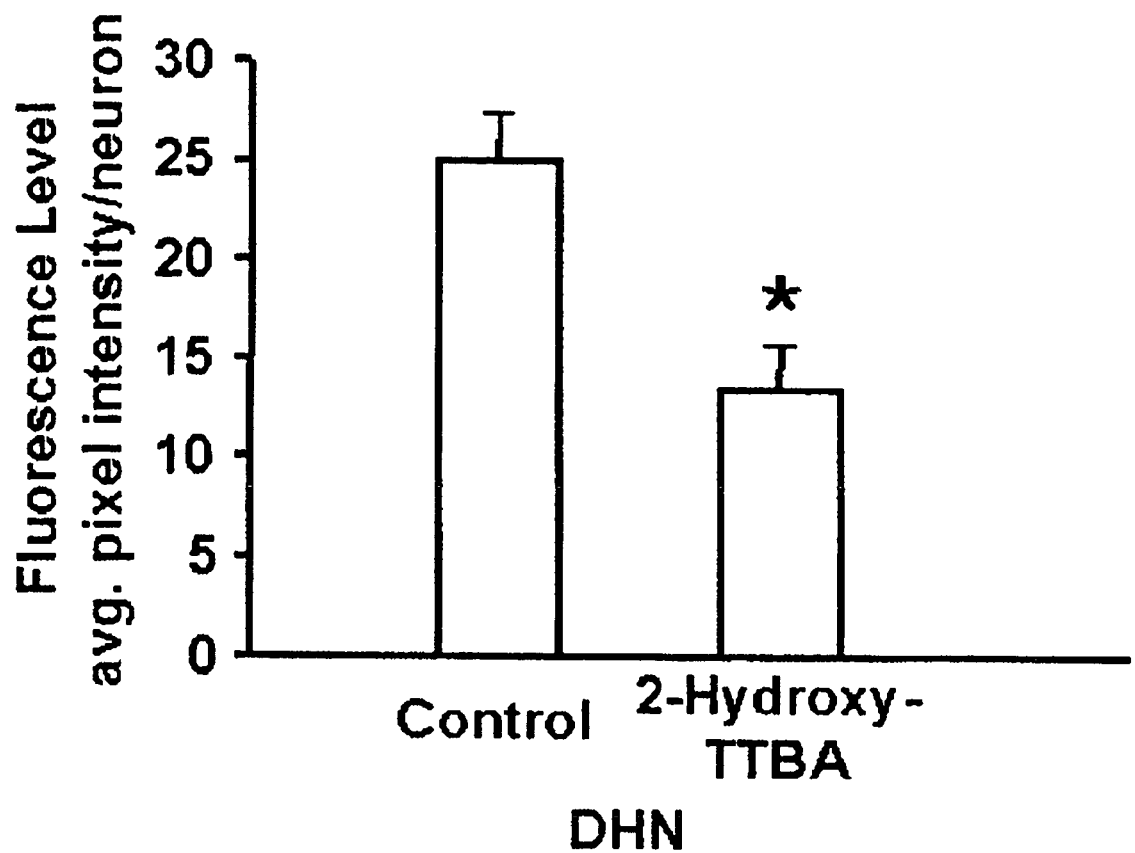

FIG. 11. 2-Hydroxy-TTBA prevents generation of mitochondrial ROS in the dorsal horn neurons of the spinal cord following traumatic injury.

Adult rats received compression injury at the level of T8 spinal cord, alone (control) or with injections of 2-Hydroxy-TTBA (50 mg/kg, ip) and Mitotracker CM-$H_2X$ ROS immediately after injury. Animals were euthanized 2 d later, spinal cord sections sections immunostained with an antibody for NeuN (a neuronal marker protein), and levels of mitochondrial ROS in the dorsal horn neurons (DHN) analyzed by measuring fluorescence intensity of oxidized Mitotracker CM-$H_2X$, mean±S.E.M. [n=12 rats for each condition (5 spinal cord sections for each rat)]. Significant difference from the vehicle control, p<0.05 using the independent t-test.

This present invention is described particularly in experimental examples using 2-Hydroxy-TTBA, 2-Hydroxy-TTS, 2-Hydroxy-TTA, 2-Chloro-TTP, 2-Ethan-TTBA, 2-Propan-TTBA and 2-Cyclohexan-TTBA manufactured in synthesis example as follows.

However, the examples described below are just representative of the present invention, which could include more examples.

EXAMPLE 1

Mixed Cortical Cell Cultures of Neurons and Glia

For mixed neuron-glia culture, mouse cerebral cortices were removed from brains of the 14-16 day-old-fetal mice (E14-16), gently triturated and plated on 24 well plates ($2\times10^5$ cells/plate) precoated with 100 μg/ml poly-D-lysine and 4 μg/ml laminine. Cultures were maintained at 37° C. in a humidified 5% $CO_2$ atmosphere. Plating media consist of Eagles minimal essential media (MEM, Earles salts, supplied glutamine-free) supplemented with 5% horse serum, 5% fetal bovine serum, 26.5 mM bicarbonate, 2 mM glutamine, and 21 mM glucose.

After 7-8 days in vitro (DIV 7-8), 10 μM cytosine arabinofuranoside (Ara-C) was included to halt overgrowth of glia. The drug treatment was carried on DIV 12-15 cortical cell culture. Overall neuronal cell injury was assessed by measuring amount of lactate dehydrogenase (LDH) released into the bathing medium 24 hr after neurotoxic insults as previously described [Koh and Choi, *J Neurosci Methods* 20:83-90, 1987].

EXAMPLE 2

Inhibitory Effects of Excitotoxicity by 2-hydroxy-TTBA, 2-hydroxy-TTA, 2-Hydroxy-TTS, 2-Ethan-TTBA, 2-Prppan-TTBA or 2-Cyclohexan-TTBA At DIV 13-15 in mixed neuron-glia culture as shown in Example 1, cortical cell cultures were exposed to 300 μM NMDA for 10 min, alone or with 3-300 μM 2-Hydroxy-TTBA, 10-300 μM 2-Hydroxy-TTS, 30-300 μM 2-Hydroxy-TTA, 30-300 μM 2-Ethan-TTBA, 10-300 μM 2-Prppan-TTBA, or 10-300 μM 2-Cyclohexan-TTBA. Neuronal death was assessed 24 hr later by measuring amount of LDH released into the bathing medium. *, Significant difference from the vehicle control, p<0.05 using ANOVA and Student-Neuman-Keuls' test.

Cortical cell cultures exposed to 300 μM NMDA for 10 min underwent widespread neuronal death (approximately 75-80% neurons died) over the next 24 hr. NMDA-induced neuronal death was blocked by co-treatment with 2-Hydroxy-TTBA in a dose-dependent manner at doses of 10-300 μM (FIG. 1*a*).

Concurrent administration of 2-Hydroxy-TTS, 2-Hydroxy-TTA, 2-Ethan-TTBA, 2-Propan-TTBA, or 2-Cyclohexan-TTBA also prevented NMDA-induced neuronal death at doses of 30-300 μM. (FIG. 1*b*).

EXAMPLE 3

Blocking Effect of 2-Hydroxy-TTBA on NMDA-Induced Inward Currents

Whole cell recordings were performed on cortical cell cultures at room temperature as described [Seo et al., *J. Pharmacol. Exp. Ther.*, 299:377-384(2001)]. Typical NMDA-induced inward currents (NMDA currents) were evoked immediately after applying 300 μM NMDA to cultured cortical neurons which were held at −70 mV. Bath application of 2-Hydroxy-TTBA immediately depressed NMDA-evoked currents in a dose dependent manner (n=7-15 neurons/condition, $IC_{50}$ value=30.55±2.96 μM) (FIG. 2*a*). Application of 100 μM 2-Hydroxy-TTBA alone had no effect on the holding currents and had little effect on the response of the cell to a subsequent treatment of 300 μM NMDA (FIG. 2*b*), suggesting that 2-Hydroxy-TTBA exerts antagonistic effect only when the NMDA receptor is activated (n=6).

EXAMPLE 4

Blockade of Oxidative Neuronal Death by 2-Hydroxy-TTBA, 2-Hydroxy-TTA, 2-Hydroxy-TTS, 2-Chloro-TTP, 2-Ethan-TTBA, 2-Propan-TTBA or 2-Cyclohexan-TTBA (4-1) Inhibition of $FeCl_2$—Induced Free Radical Toxicity Mixed cortical cell cultures (DIV 13-15) were continuously exposed to 50 μM $FeCl_2$, which produces hydroxyl radical via a Fenton reaction, alone or with inclusion of 2-Hydroxy-TTBA, 2-Hydroxy-TTA, 2-Hydroxy-TTS, 2-Chloro-TTP, 2-Ethan-TTBA, 2-Propan-TTBA, 2-Cyclohexan-TTBA or trolox (a vitamin E analogue) at indicated doses. Neuronal cell death was analyzed 24 hr later by LDH assay as described above. *, Significant difference from the vehicle control ($FeCl_2$), p<0.05 using ANOVA and Student-Neuman-Keuls' test.

Cortical cell cultures exposed to $FeCl_2$ underwent widespread neuronal death over the next 24 hr. 2-Hydroxy-TTBA and trolox prevented $FeCl_2$-induced free radical neurotoxicity in a dose-dependent manner. However, 2-Hydroxy-TTBA was 30-fold stronger than trolox in preventing free radical neurotoxicity (FIG. 3*a*). Moreover, synthetic derivatives of 2-Hydroxy-TTBA (2-Hydroxy-TTS, 2-Hydroxy-TTA, 2-Chloro-TTP, 2-Ethan-TTBA, 2-Propan-TTBA, or 2-Cyclohexan-TTBA) showed much stronger neuroprotective effects than trolox in preventing. $FeCl_2$-induced free radical neurotoxicity (FIG. 3*b*).

(4-2) Inhibition of SNP (Sodium Nitroprusside) Cytotoxicity

Mixed cortical cell cultures were continuously exposed to 5 μM SNP, a nitric oxide (NO) donor, alone or with inclusion of 0.1-10 μM 2-Hydroxy-TTBA, 1-10 μM trolox or 100-10, 000 μM aspirin. Neuronal cell death was analyzed 24 hr later by LDH assay. *, Significant difference from the vehicle control (SNP), p<0.05 using ANOVA and Student-Neuman-Keuls' test.

Administration of SNP resulted in complete neuronal cell death and some glial cell death. SNP toxicity was completely blocked in the presence of 2-Hydroxy-TTBA and trolox. The former was 100-fold stronger than the latter in preventing NO toxicity. Aspirin, a structural component of 2-Hydroxy-TTBA, did not reduce SNP cytotoxicity (FIG. 4).

(4-3) Inhibition of Zinc Neurotoxicity

To induce zinc ($Zn^{2+}$) neurotoxicity, mixed cortical cell cultures were exposed to 100 μM $ZnCl_2$ for 30 min in a HEPES-buffered control salt solution (HCSS): (in mM) 120 NaCl, 5 KCl, 1.6 $MgCl_2$, 2.3 $CaCl_2$, 15 glucose, 20 HEPES and 10 NaOH, alone or with 3-300 uM 2-Hydroxy-TTBA. After exposure, cultures were washed out 3 times and exchanged with MEM adjusted to 25 mM glucose and 26.2 mM sodium bicarbonate. Neuronal cell death was analyzed 24 hr later by LDH assay. *, Significant difference from the vehicle control (SNP), p<0.05 using ANOVA and Student-Neuman-Keuls' test.

Concurrent treatment with 2-Hydroxy-TTBA prevented zinc-induced neuronal death in a dose-dependent manner at doses of 10-300 μM (FIG. 5).

(4-4) DPPH Assay of 2-Hydroxy-TTBA, 2-Hydroxy-TTA, 2-Hydroxy-TTS or 2-Chloro-TTP To examine the free radical scavenging effects, 1-100 µM 2-Hydroxy-TTBA, 2-Hydroxy-TTA, 2-Hydroxy-TTS, 2-Chloro-TTP or trolox was reacted with 100 µM DPPH (2,2-diphenyl-1-picryl-hydrazyl radical), a stable free radical, dissolved in ethanol. After incubation for 30 min, relative decrease in DPPH absorption at 517 nm was measured by a spectrophotometer, mean±SEM (n=3 test tubes per condition). *, Significant difference from the vehicle control (DPPH alone), p<0.05 using ANOVA and Student-Neuman-Keuls' test.

Compared to the anti-oxidant trolox, 2-Hydroxy-TTBA reduced levels of DPPH at lower doses, suggesting that 2-Hydroxy-TTBA is a direct anti-oxidant stronger than trolox (FIG. 6a). Other synthetic derivatives also reduced levels of DPPH (FIG. 6b).

EXAMPLE 5

Prevention of Neuronal Cell Death in Spinal Cord of ALS Mouse by 2-hydroxy-TTBA

Transgenic mice with the G93A human SOD1 mutation (B6SJL-TgN(SOD1-G93A)1Gur), animal models of ALS (ALS mice) were obtained from Jackson Laboratories (ME, USA). 2-hydroxy-TTBA was administered to 2 month-old wild type and ALS transgenic mice through drinking water bottle (10 mg/kg per day) for 8 weeks. Animals were then euthanized and spinal cords processed for histological examination by staining with hematoxylin and eosin. Spinal motor neurons from ALS mice without being treated with 2-hydroxy-TTBA (control) underwent degeneration as evident by eosinophilic staining, which was reduced in ALS mice treated with 2-hydroxy-TTBA (FIG. 7a).

The number of degenerating neurons was analyzed by counting eosinophilic neurons in ventral horn (VH) and dorsal horn (DH). Administration of 2-hydroxy-TTBA significantly prevented degeneration of dorsal and ventral horn neurons in the spinal cord from ALS mice (FIG. 7b). *, Significant difference from the control, p<0.05 using independence t test.

EXAMPLE 6

Prevention of Hypoxic-Ischemic Brain Injury by 2-Hydroxy-TTBA (6-1) Induction of Transient Focal Cerebral Ischemia in Rat Sprague-Dawley rats were anesthetized with chloral hydrate, and subjected to focal cerebral ischemia by occlusion of middle cerebral artery (MCAO) as previously described [Tamura et al., J. Cerebr. Blood Flow Metab. 1:53-60(1981)]. Both common carotid arteries (CCAs) were exposed and right middle cerebral artery (rMCA) was exposed under the surgical microscope by making a 3 mm diameter craniotomy rostral to the foramen ovale. CCAs and rMCA were occluded with microclips. The clips were released 60 min later and restoration of blood flow in rMCA was observed under the microscope (6-2) 2-Hydroxy-TTBA Reduces Infarct Volume after 60 min MCAO.

Animals received MCAO for 60 nm, alone or with administration of 2-Hydroxy-TTBA (50 mg/kg, i.p.) at indicated points of time after reperfusion. Saline was injected as a control. Animals were euthanized. 24 hr later and brains removed and sectioned coronally into seven 2-mm slices in a brain matrix. Brain slices were placed in 2% 2,3,5,-triphenyltetrazolium chloride solution, followed by 10% formalin overnight. The infarction area, outline in white, was measured (TINA image analysis system) and infarction volume was calculated by summing the infarct volume showing white of sequential 2-mm-thick section, mean±SEM (n=8-12 rats/condition) (FIG. 8a). Note that delayed administration (ip) of 2-Hydroxy-TTBA up to 1 hr after reperfusion significantly reduced infarct volume. Higher doses of 2-Hydroxy-TTBA (100 mg/kg, ip) also showed similar protection against 60 min MCAO (FIG. 8b).

Additional experiments were performed to examine effects of intravenous injections of 2-Hydroxy-TTBA (5 mg/kg) against 60 min MCAO. 2-Hydroxy-TTBA was administered at indicated points of time after reperfusion. The delayed injections of 2-Hydroxy-TTBA up to 4 hr after reperfusion significantly attenuated infarct volume evolving 24 hr after 60 min MCAO, mean±SEM (n=8-12 ratS/condition) (FIG. 8c).

Dose-response experiments of the intravenous injections of 2-Hydroxy-TTBA showed that 2-Hydroxy-TTBA attenuated infarct volume at doses as low as 1 mg/kg. The protective effects of 2-Hydroxy-TTBA were observed at doses higher than 2.5 mg/kg, mean±SEM (n=8-12 rats/condition) (FIG. 8d).

Protective effects of 2-Hydroxy-TTBA were also verified through oral administration. In particular, administration of 2-Hydroxy-TTBA (10 or 20 mg/kg, p.o.) at 5 min after reperfusion reduced infarct volume 24 hr after 60 min MCAO, mean±SEM (n=8-12 ratS/condition) (FIG. 8e).

EXAMPLE 7

Prevention of the CA1 Neuronal Cell Death after Transient Forebrain Ischemia by 2-Hydroxy-TTBA (7-1) Induction of Global Ischemia in Rat Male adult Sprague-dawley rats (250-300 g) were anesthetized with chloral hydrate and subjected to four-vessel occlusion model (occlusion of both common carotid arteries and vertebral arteries) as previously described (Pulsinelli and Brierley, stroke 10: 267-272 (1979)].

(7-2) Inhibition of Mitochondrial ROS Generation after Global Ischemia by 2-Hydroxy-TTBA Rats received the intracerebroventricular injections of 0.4 nmol Mitotracker CM-$H_2$X Ros. After 24 hr, rats received four-vessel occlusion for 10 min. Immediately after reperfusion, rats received the intraperitoneal injections of saline (control) or 2-Hydroxy-TTBA (50 mg/kg). Levels of mitochondrial ROS were analyzed 2 hr later by measuring the fluorescence intensity of oxidized Mitotracker CM-$H_2$X Ros in mitochondria. Administration of 2-Hydroxy-TTBA reduced production of mitochondrial ROS 2 hr after transient global ischemia (FIG. 9a).

(7-3) Inhibition: of Neuronal Cell Death in the CA1 Field Following Transient Forebrain Ischemia by 2-Hydroxy-TTBA Rats received four-vessel occlusion for 10 min followed by administration of saline (control) or 2-Hydroxy-TTBA (50 mg/kg, ip) Animals were euthanized 3 d later and processed for analysis of neuronal death in the CA1 field after staining with hematoxylin and eosin(mean±SEM, N=12 rats/condition). Administration of 2-Hydroxy-TTBA prevented delayed neuronal cell death in the CA1 areas evolving after transient global ischemia (FIG. 9b). *, Significant difference from the control, p<0.05 using independence t test.

EXAMPLE 8

Prevention of Dopaminergic Neuronal Cell Death in the Substantial Nigra Following the Injection of MPTP (1-methyl-4-phenyl-1,2,3,6-tetra-hydropyridine) by 2-Hydroxy-TTBA (8-1) Inhibition of Dopaminergic Neurons by 2-Hydroxy-TTBA C57/BL6 mice (male, 8 weeks) received the injections of 40 mg/kg MPTP (s.c.), alone or with 25 or 50 mg/kg 2-Hydroxy-TTBA (ip) every 12 hr per day beginning 30 min before MPTP injection. After 3 or 7 days, all animals were anesthetized with chloral hydrate and perfused transcardially with PBS followed by 4% paraformaldehyde. Brains were immediately removed and immersed in the fixative for 8-10 h. The fixative was replaced with 30% sucrose, incubated at 4° C. for 2 d, and stored at −70° C. The brains were sectioned at a thickness of 30 μm on a sliding microtome (TPI, Inc., MO). Sections were then stored in 0.1 M phosphate buffer (pH 7.4, 0.30% (v/v) glycerol, 30% ethylene glycol) at 4° C. until use. The sections were immunostained with anti-TH (tyrosine hydroxylase) antibody, colored by DAB (diaminobenzidine), and then observed under light microscope to analyze the degeneration of dopaminergic neurons.

Mice treated with MPTP showed marked degeneration of the dopaminergic neurons in the substantia nigra over the next 3 d. The intraperitoneal injections of 2-Hydroxy-TTBA significantly attenuated degeneration of the dopaminergic neurons (FIGS. 10a and 10b). The protective effects of 2-Hydroxy-TTBA are also observed at 7 d following administration of MPTP (FIG. 10c and

EXAMPLE 9

Inhibition of Mitochondrial ROS Production in the Spinal Cord after Traumatic Spinal Cord Injury Sprague-Dawley rats (250-300 g, female) received traumatic spinal cord injury by compression of the dorsal spinal cord T8 segment of spinal cord was exposed on the dorsal side, compressed with 20 g for 10 min, and then mitochondrial CM-H$_2$X Ros was immediately injected into the spinal cord. 2-Hydroxy-TTBA (50 mg/kg, ip) or a vehicle control (control) was injected with mitochondrial CM-H$_2$X Ros. Levels of mitochondrial ROS in the dorsal horn neurons were analyzed 48 hr later as described above after immunolabeling with anti-NeuN antibody, a neuron-specific marker. Administration of 2-Hydroxy-TTBA significantly reduced mitochondrial ROS production in the spinal cord neurons after the traumatic spinal cord injury (FIG. 11) (mean±SEM, N=12 rats/condition). *, Significant difference from the control, p<0.05 using independence t test.

As described above, tetrafluorobenzyl derivatives or its pharmaceutically-acceptable salts in the present invention can be used as NMDA receptor antagonists, anti-oxidants, and inhibitors of zinc neurotoxicity.

The concrete diseases applicable with tetrafluorobenzyl derivatives or its pharmaceutically-acceptable salts are described as follows.

Application examples described below are part of examples of this invention. This invention is not limited to application examples.

APPLICATION EXAMPLE 1

Stroke

Interrupted blood supply to brain or stroke induces neuronal death primarily through over-activation of $Ca^{2+}$-permeable glutamate receptor induced by accumulation of glutamate, an excitatory neurotransmitter, in synaptic cleft. It has been well documented that NMDA receptor antagonists decrease the neuronal cell death by ischemic stroke accounting for 80% of stroke [Simon et al., *Science*, 226: 850-852 (1984); Park et al., *Ann Neurol.*, 24:543-551 (1988); Wieloch, *Science*, 230:681-683 (1985); Kass et al.; *Exp. Neurol.*, 103:116-122 (1989); Weiss et al., *Brain Res.*, 380:186-190 (1986)]. It has also been reported that ROS and zinc are main mechanism of neuronal death following stroke. Anti-oxidants or inhibitors of zinc toxicity protect ischemic injury in animal models of stroke [Flamm, E. S. et al., *Stroke*, 9(5):445-447(1978); Kogure, K. et al., *Prog. Brain Res.*, 63:237-259(1985); Chan, P. H., *J. Neurotrauma.*, 9 suppl2:S417-423(1992)]. Therefore, the compounds in the present invention showing multiple protective effects against excitotoxicity, oxidative stress, and zinc toxicity can be used as therapeutic drugs for stroke.

APPLICATION EXAMPLE 2

Trauma

Excitotoxins are closely related to the degeneration of neuronal cells following traumatic brain injury (TBI) and traumatic spinal cord injury (TSCI). quinolinic acid, an NMDA receptor agonist present in human body, is increased 50 to 500 times in TBI patients [Sinz et al., *J. Cereb. Blood Flow Metab.*, 18:610-615 (1988)]. It has been reported that NMDA receptor antagonists decrease the neuronal death following TBI and TSCI [Faden et al., *J Neurotrauma*, 5:33-45 (1988); Okiyama et al., *J Neurotrauma*, 14:211-222 (1997)]. Anti-oxidants also inhibit tissue damage following TBI or TSCI [Faden & Salzman, *Trends Pharmacol. Sci.*, 13:29-35(1992)]. Therefore, the compounds in the present invention showing multiple protective effects against excitotoxicity and oxidative stress can be used as therapeutic drugs for TBI and TSCI.

APPLICATION EXAMPLE 3

Epilepsy

Administration of kainate, an agonist of AMPA and kainate glutamate receptors, induces seizure and neuronal cell death in several brain areas including the hippocampal formation. NMDA receptor antagonists were shown to inhibit convulsion and seizure in several epileptogenic animal models [Anderson et al., *J. Neurophysiol*, 57:1-21 (1987); Wong et al., *Neurosci Lett.*, 85:261-266 (1988); Mc Namara et al., *Neuropharmacology*, 27:563-568 (1988)]. Anti-oxidants inhibit seizure and seizure-induced neuronal death [He et al., *Free Radic. Biol. Med.* 22:917-922(1997); Kabuto et al., *Epilepsia*, 39:237-243(1998)]. Therefore, the compounds in the present invention showing multiple protective effects against excitotoxicity and oxidative stress can be used as therapeutic drugs for epilepsy and seizure-induced neuronal death.

APPLICATION EXAMPLE 4

Amyotrophic Lateral Sclerosis

ALS patients show increased levels of extracellular glutamate and defects in glutamate transport in astrocytes. Administration of glutamate receptor agonists into the spinal cord mimicked pathological changes in the spinal cord of ALS patients [Rothstein et al., *Clin Neurosci.*, 3:348-359 (1995); Ikonomidou et al., *J Neuropathol Exp Neurol*, 55:211-224 (1996)]. Besides excitotoxicity, evidence is being accumulated that oxidative stress is involved in neuronal death in ALS [Cookson & Shaw, *Brain Pathol.*, 9:165-186(1999)]. In fact, the major pharmacological action of riluzole, the new drug for ALS patients that received FDA approval, involves prevention of excitotoxicity and oxidative stress [Obrenovitch, *Trends. Pharmacol. Sci.* 19:9-11 (1998); Noh et al. *Neurobiol. Dis.*, 7:375-383(2000)]. Therefore, the compounds in the present invention showing multiple protective effects against excitotoxicity and oxidative stress can be used as therapeutic drugs for ALS.

APPLICATION EXAMPLE 5

Parkinson's Disease (PD)

PD is a neurodegenerative disease showing the disorder of motor function by a selective death of dopaminergic neurons in the substantia nigra. Several antagonists of NMDA receptors protect dopaminergic neurons from the dopaminergic neurotoxin MPTP (1-methyl-4-phenyl-1,2,3,6-tetrahydropyridine) [Lange et al., *Naunyn Schmiedebergs Arch. Pharmacol.* 348:586-592 (1993); Brouillet and Beal. *Neuroreport.* 4:387-390 (1993)]. NMDA receptor antagonists also ameliorate levodopa-induced dyskinesia and thus can improve the therapeutic effects of levodopa [Papa and Chase, *Ann. Neurol.* 39:574-578 (1996); Marin et al., *Brain Res.* 736: 202-205 (1996)]. Oxidative stress as well as exitotoxicity has been proved as a main mechanism of neuronal cell death in PD patients [Schapira et al., biochem. *Soc. Trans.*, 21:367-370(1993)]. Therefore, the compounds in the present invention showing multiple protective effects against excitotoxicity and oxidative stress can be used as therapeutic drug for PD.

APPLICATION EXAMPLE 6

Huntington's Disease (HD)

HD is a progressive neurodegenerative disease predominantly affecting small- and medium-sized interneurons in the striata. These pathological features of HD are observed in vivo and in vitro following administration of NMDA receptor agonists, raising the possibility that NMDA receptor-mediated neurotoxicity contributes to selective neuronal death in HD [Koh et al., *Science* 234:73-76 (1986); Beal et al., *Nature* 321:168-171 (1986); Beal et al., *J. Neurosci.* 11:1649-1659 (1991)]. Since evidence is being accumulated that oxidative stress, such as mitchondrial dysfunction and generation of ROS, causes neuronal death observed in PD, it is possible that the drugs inhibiting ROS are used for therapy of HD [Jenner, *Pathol. Biol.* 44:57-64(1996); Albers & Beal, *J. Neural. Transm. Suppl.*, 59:133-154(2000)]. Therefore, the compounds in the present invention showing multiple protective effects against excitotoxicity and oxidative stress can be used as therapeutic drugs for HD.

APPLICATION EXAMPLE 7

Alzheimer's Disease (AD)

The degeneration of glutamatergic neurons in the cerebral cortex and hippocampal formation and of cholinergic neurons in the basal forebrain, extracellular deposit of amyloid plaque, and intracellular neurofibrillary tangles are pathological features of AD. In AD, the production of lipid peroxidation, 8-hydroxy deoxyguanosine, protein carbonyls, nitration, or oxidative crosslinking of proteins by excess generation of free radicals has been reported, suggesting that oxidative stress plays a causative role in neuronal death in AD [Vitek et al., *Proc. Natl. Acad. Sci. U.S.A.*, 91:4766-4770 (1994); Smith et al., *Trends. Neurosci.*, 18:172-176 (1995), *Mol. Chem. Neuropathol.*, 28:41-48 (1996), *Proc. Natl. Acad. Sci. U.S.A.*, 94:9866-9868 (1997); Montine et al., *J. Neuropathol. Exp. Neurol.*, 55:202-210 (1996)]. As a matter of fact, the therapeutic effects of anti-oxidants have been extensively investigated in AD patients. $Zn^{2+}$ is accumulated in the brain (amygdala, hippocampus, inferior parietal lobule, superior and middle temporal gyri) of AD patients, mainly in the center and surround of amyloid plaque and induces aggregation of beta amyloid [Bush et al., *Science* 265:1464-1467 (1994); Lovell et al., *J. Neurol. Sci.*, 158:47-52 (1998)]. Therefore, the compounds in the present invention showing protective effect against oxidative stress and $Zn^{2+}$ toxicity can be used as therapeutic drugs for AD.

APPLICATION EXAMPLE 8

Ocular Diseases and Cataract

In glaucoma, the increased intraocular pressure blocks blood flow into retina, causes retinal ischemia, and induces excessive release of glutamate into synaptic cleft. Once released, glutamate induces NMDA receptor-mediated excitotoxicity by opening calcium channels and increasing intracellular $Ca^{2+}$ concentration in post-synaptic neurons. The degeneration of retina cells can also occur through the increased generation of reactive oxygen species during reperfusion [Osborne N. N. et al., *Surv. Opthalmol.*, 43 suppl., 1:S102-28 (1999); Hartwick A. T., *Optom. Vis. Sci.*, 78:85-94 (2001)]. Administration of NMDA receptor antagonists or anti-oxidants inhibits retinal degeneration in animal model of glaucoma [Gu. Z. et al., *Nippon Ganka Gakkai Zasshi*, 104:11-6 (2000); Vorwerk C. K. et al., *Surv Ophthalmol.*, 43 suppl., 1:S142-50 (1999); Schwartz M. et al.,. *Eur. J. Ophthalmol.*, 9 Suppl., 1:S9-11 (1999)].

In cases of retinopathy and macular degeneration, neuronal degeneration can be blocked by inhibition of excitotoxicity and oxidative stress, main causes of these diseases [Lieth E. et al., *Clin. Experiment Ophthalmol.*, 28(1):3-8 (2000); Moor P. et al., *Exp. Eye Res.*, 73:45-57 (2001); Winkler B. S. et al., *Mol. Vis.*, 5:32 (1999); Simonelli F. et al., *Clin. Chim. Acta.*, 320:111-5 (2002)].

Cataract is a senile disease accompanying lenticular opacity. Oxidative stress has been considered as a primary mediator of cataract. In fact, anti-oxidants have been applied to treat cataract [Varma et al., *Curr. Eye Res.* 3:35-57(1984); Anderson et al., *Adv. Exp. Med. Biol.*, 366:73-86(1994)].

Therefore, the compounds in the present invention showing multiple protective effects against excitotoxicity and oxidative stress can be used as therapeutic drugs for ocular diseases.

APPLICATION EXAMPLE 9

Drug Addiction

The activation of mesolimbic dopaminergic neurons in the ventral tagmental area that project to the nucleus accumbens is essential for the process of drug addition that requires neuronal excitability [Self D. W. and Nestler E. J., *Annu. Rev. Neurosci.*, 18:463-95 (1995)]. Several lines of evidence supports that NMDA receptor antagonists can be applied to reduce neuronal adaptability to abused drugs and have been suggested as new therapeutic agents for drug addiction [Boening et al., *Alcohol Clin. Exp. Res.*, 25:127S-131S (2001); Vorel et al., *Science*, 292:1175-8 (2001)].

APPLICATION EXAMPLE 10

Depression

Tricyclic antidepressants and MAO (monoamine oxidase) inhibitors, antidepressants, increase neurotransmission of noradrenaline and serotonin. The existing therapeutic drugs induce a lot of side effects through interacting with other nervous system and have no therapeutic effect in 30% of depressed patients [Pacher et al., *Curr. Med. Chem.*, Feb. 8 (2):89-100 (2001)]. Recently, NMDA receptor antagonists were shown to be applicable as new therapeutic drugs for depression [Le D. A. and Lipton S. A., *Drugs Aging*, 18:717-724 (2001); Petrie et al., *Pharmacol. Ther.*, 87:11-25 (2000)].

APPLICATION EXAMPLE 11

Pain

Neuropathic pain results from the increased neurotransmission following peripheral injury and neural tissues damage in relation with surgery, cancer patients, and trauma etc [Hempenstall K. and Rice A. S., *Curr. Opin. Investig. Drugs.*, March; 3 (3):441-8 (2002); McDonnell et al., *Curr. Oncol. Rep.*, 2:351-7 (2000)]. Since the activation of NMDA receptor is necessary for the processing of neuropathic pain, it has been reported that NMDA receptor antagonists can be used as therapeutic drugs to treat neuropathic, pain [Parson C. G., *Eur. J. Pharmacol.*, 429:71-8 (2001); Hewitt, *Clin. J. Pain.*, 16:S73-9 (2000)].

APPLICATION EXAMPLE 12

Multiple Sclerosis, Meningitis, Encephalitis or Hydrocephalus

Oxidative stress plays a role in the pathogenesis of multiple sclerosis, meningitis, encephalitis, and hydrocephalus. Levels of anti-oxidants such as retinal, a-tocopherol, b-carotene and ascorbic acid are reduced in the body of multiple sclerosis patients [Calabrese, V et al., *Int. J. Clin. Pharmacol. Res.*, 14(4):119-123(1994); Besler H. T. et al., *Nutr. Neurosci.* 5(3):215-220(2002); *Nutr. Neurosci.* 6(3): 189-196(2002)]. Increased ROS generation and neuronal cell death are observed at meningitis patient and its animal model [Maurizi C. P., *Med. Hypotheses*, 52(1):85-87(1999); Christen S. et al., *Free Radic. Biol. Med*, 31(6):754-762 (2001); Kastenbauer S. et al., *Neurology*, 58(2)186-191 (20.02)], infection model by encephalitis virus [Fujii, S. et al., *Virology*, 256(2):203-212(1999); Raung S. L. et al., *Neurosci. Lett.*, 315(1-2):9-12(2001)], and hydrocephalus patients [Nuss J. I. et al., *Am. J. Vet Res.*, 28(127):1909-1913(19.67); Vannucci R. C. et al., *Dev. Med. Child. Neurol.*, 22(3):308-316(1980); Radwanska-Wala B. et al., *Pathol. Res. Pract.*, 198(6):421-423(2002)]. Therefore, the compounds in the present invention showing protective effect against oxidative stress can be used as therapeutic drugs for neuronal death induced by multiple sclerosis, meningitis, encephalitis or hydrocephalus.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

INDUSTRIAL APPLICABILITY

As described hereinbefore, Tetrafluorobenzyl derivatives or pharmaceutically-acceptable salts, and pharmaceutical composition containing the same as the effective component can prevent and treat the neurodegenerative diseases such as amyotrophic lateral sclerosis, Parkinson's diseases, Huntington's disease or Alzheimer's disease, the convulsive neuronal diseases such as epilepsy etc, and brain injury by stroke, trauma, or hydrocephalus, ocular diseases by glaucoma and retinopathy, mental diseases by drug addiction and depression, neuropathic pain, inflammatory diseases by meningitis and encephalitis as described above.

What is claimed is:

1. A tetrafluorobenzyl derivative represented by the following chemical formula:

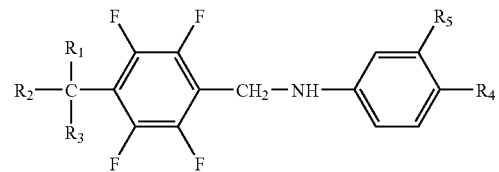

wherein, $R_1$, $R_2$ and $R_3$ are hydrogen or halogen, $R_4$ is hydroxy, alkoxy or alkoxy substituted with halogen, and $R_5$ is carboxyl acid or ester having $C_1$-$C_4$; or a pharmaceutically acceptable salt thereof.

2. The tetrafluorobenzyl derivative or its pharmaceutically acceptable salt according to claim 1, wherein $R_1$, $R_2$ and $R_3$ are halogen.

3. The tetrafluorobenzyl derivative or its pharmaceutically acceptable salt according to claim 2, wherein halogen is fluoride.

4. The tetrafluorobenzyl derivative or its pharmaceutically acceptable salt according to claim 1, wherein $R_4$ is hydroxy.

5. The tetrafluorobenzyl derivative or its pharmaceutically acceptable salt according to claim 1, wherein $R_5$ is carboxyl acid.

6. The tetrafluorobenzyl derivative or its pharmaceutically acceptable salt according to claim 1, wherein $R_1$, $R_2$ and $R_3$ are halogen, $R_4$ is hydroxy and $R_5$ is carboxyl acid.

7. A pharmaceutical composition comprising a tetrafluorobenzyl derivative or its pharmaceutically acceptable salt according to claim 1, and a pharmaceutically acceptable carrier, diluent or excipient.

8. A pharmaceutical composition comprising a tetrafluorobenzyl derivative or its pharmaceutically acceptable salt according to claim 2, and a pharmaceutically acceptable carrier, diluent or excipient.

9. A pharmaceutical composition comprising a tetrafluorobenzyl derivative or its pharmaceutically acceptable salt according to claim 3, and a pharmaceutically acceptable carrier, diluent or excipient.

10. A pharmaceutical composition comprising a tetrafluorobenzyl derivative or its pharmaceutically acceptable salt according to claim 4, and a pharmaceutically acceptable carrier, diluent or excipient.

11. A pharmaceutical composition comprising a tetrafluorobenzyl derivative or its pharmaceutically acceptable salt according to claim 5, and a pharmaceutically acceptable carrier, diluent or excipient.

12. A pharmaceutical composition comprising a tetrafluorobenzyl derivative or its pharmaceutically acceptable salt according to claim 6, and a pharmaceutically acceptable carrier, diluent or excipient.

13. A pharmaceutical composition comprising a tetrafluorobenzyl derivative and a pharmaceutically acceptable carrier, diluent or excipient, wherein the tetrafluorobenzyl derivative is 2-hydroxy-5-(2,3,5,6-tetrafluoro-4-trifluoromethyl-benzylamino)-benzoic acid or a pharmaceutically acceptable salt thereof.

14. The composition of claim 13 wherein the tetrafluorobenzyl derivative is a pharmaceutically acceptable salt of 2-hydroxy-5-(2,3,5,6-tetrafluoro-4-trifluoromethyl-benzylamino)-benzoic acid.

15. The composition of claim 13 wherein the tetrafluorobenzyl derivative is 2-hydroxy-5-(2,3,5,6-tetrafluoro-4-trifluoromethyl-benzylamino)-benzoic acid.

* * * * *